United States Patent [19]
Parce et al.

[11] Patent Number: 5,496,697
[45] Date of Patent: * Mar. 5, 1996

[54] METHODS AND APPARATUS FOR DETECTING THE EFFECT OF CELL AFFECTING AGENTS ON LIVING CELLS

[75] Inventors: John W. Parce; Harden M. McConnell, both of Palo Alto; Gillian M. K. Humphries, Los Altos; Karen M. Kercso, Menlo Park; John C. Owicki; Josef E. Kercso, both of Palo Alto, all of Calif.

[73] Assignee: Molecular Devices Corporation, Sunnyvale, Calif.

[*] Notice: The portion of the term of this patent subsequent to Jan. 11, 2011, has been disclaimed.

[21] Appl. No.: 118,094

[22] Filed: Sep. 8, 1993

Related U.S. Application Data

[63] Continuation of Ser. No. 833,602, Feb. 11, 1992, abandoned, which is a continuation of Ser. No. 408,896, Sep. 18, 1989, abandoned, which is a continuation-in-part of Ser. No. 260,521, Oct. 21, 1988, abandoned.

[51] Int. Cl.$^6$ .............................. C12Q 1/02; C12Q 1/70
[52] U.S. Cl. ................... 435/5; 435/29; 435/32; 435/34; 435/817
[58] Field of Search ................... 435/5, 7.1, 29, 435/32, 34, 817, 948

[56] References Cited

U.S. PATENT DOCUMENTS

| | | | |
|---|---|---|---|
| 4,055,799 | 10/1977 | Coster et al. | 324/71 R |
| 4,129,483 | 12/1978 | Bochner | 195/100 |
| 4,204,037 | 5/1980 | Dill et al. | 435/3 |
| 4,220,916 | 9/1980 | Zimmermann et al. | 324/71 R |
| 4,235,964 | 11/1980 | Bochner | 435/34 |

(List continued on next page.)

FOREIGN PATENT DOCUMENTS

| | | | |
|---|---|---|---|
| 79300609 | 10/1979 | European Pat. Off. | G01N 33/16 |
| 82101917 | 1/1982 | European Pat. Off. | C12M 3/02 |
| 87305456 | 4/1987 | European Pat. Off. | G01N 27/07 |
| 87200535 | 9/1987 | European Pat. Off. | G01N 33/52 |
| 88200926 | 6/1988 | European Pat. Off. | C12M 1/40 |
| 595441 | 2/1978 | Switzerland | C12N 1/20 |
| 1414076 | 11/1975 | United Kingdom | C12K 9/00 |
| WO85/02017 | 5/1985 | WIPO . | |

OTHER PUBLICATIONS

Szejda, P. et al. (1984) J. Immunol 133: 3303–3307.
Briggs, et al. (1985) J. Immunol. Meth. 81: 73–81.
Brunette (1986) Exp. Cell Res. 164: 11–26.
Diamond, et al. (1978) Journal of Biological Chemistry 253: 866–871.
Ekwall (1980) Toxicol. Lett. 5: 309–317.
Ekwall (1980) Toxicology 17: 273–295.
Grattarola et al. (1989) Proc. IEEE Eng. in Med. & Biol. Soc. 11: 1346–1347.
Grattarola, et al. (1988) Biomaterials 9: 101–106.
Hafeman, et al. (1988) Science 240: 1182–1185.
Hafeman, et al. (1984) Biochimica et Biophysica Acta 772: 20–28.
Handler, et al. (1984) Federation Proceedings 43: 2221–2224.
Hultborn, et al. (1985) Acta Physiol. Scand. 124: 5–10.
Karube, et al. (1979) Analytica Chimica Acta 109: 39–44.
Kleinfeld, D. et al. (1988) J. Neurosci. 8: 4098–4120.
Li, et al. (1988) Biotechnol. Bioeng. 31: 250–256.
Li, et al. (1988) Computers Biol. Med. 18: 367–376.

(List continued on next page.)

*Primary Examiner*—Ralph J. Gitomer
*Attorney, Agent, or Firm*—Banner & Allegretti, Ltd.

[57] ABSTRACT

Methods and apparatus are disclosed for detecting the effects of cell affecting agents on living cells. The method steps include providing living cells that are retained in a micro flow chamber. The micro flow chamber is adapted for either continuous or intermittent flow of solutions or suspensions in intimate contact with the cells. The solutions or suspensions, which contain a cell affecting agent, are then flowed in intimate contact with the cells and the pit is measured.

3 Claims, 26 Drawing Sheets

U.S. PATENT DOCUMENTS

| | | | |
|---|---|---|---|
| 4,299,669 | 11/1981 | Obana et al. | 204/1 T |
| 4,350,763 | 9/1982 | Suzuki et al. | 435/29 |
| 4,386,157 | 5/1983 | Nishioka | 435/34 |
| 4,428,669 | 1/1984 | Bessis | 356/39 |
| 4,512,853 | 4/1985 | Wright et al. | 240/1 T |
| 4,519,890 | 5/1985 | Uematsu et al. | 204/409 |
| 4,560,881 | 12/1985 | Briggs | 250/458.1 |
| 4,564,598 | 1/1986 | Briggs | 436/501 |
| 4,591,550 | 5/1986 | Hafeman et al. | 435/4 |
| 4,704,353 | 11/1987 | Humphries et al. | 435/4 |
| 4,732,811 | 3/1988 | Margel | 428/403 |

OTHER PUBLICATIONS

PCT Application No. PCT/SE82/00193 (Mattiasson) 1982.

Meisner, et al. (1977) J. Lipid Res. 18: 774–776.

Moolenaar (1986) Ann. Rev. Physiol. 48: 363–376.

Nilsson, et al. (1979) J. Lipid. Res. 20: 557–560.

Regehr, et al. (1988) IEEE Trans. Biomed. Eng. 35: 1023–1032.

Reuss, et al. (1984) in Forte, J., et al., eds. Hydrogen Ion Transport in Epithelia, pp. 85–96.

Schon, et al. (1986) J. Biochem. Biophys. Meth. 13: 135–143.

Schon, et al. (1988) Cytobios 55: 33–39.

Selling, et al. (1985) Xenobiotica 15: 713–717.

Simpson, et al. (1982) Analytical Letters 15: 1345–1359.

Weinbach, et al (1985) Cancer Letters 26: 253–259.

Wenzel, et al. (1983) Toxicology 29: 173–182.

Zeuthen, et al. (1984) in Forte, J., et al., eds. Hydrogen Ion Transport in Epithelia, pp. 97–108.

Rawson et al. (1989), Biosensor 4: 299–311.

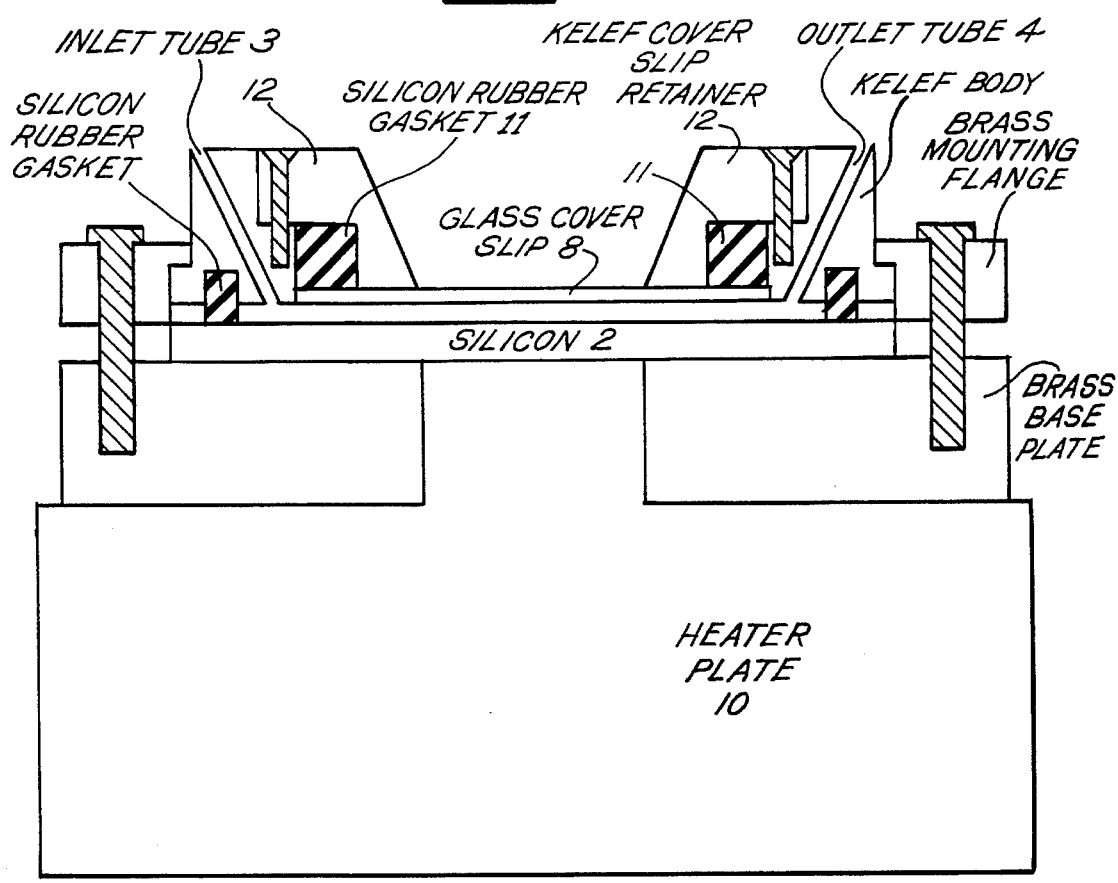

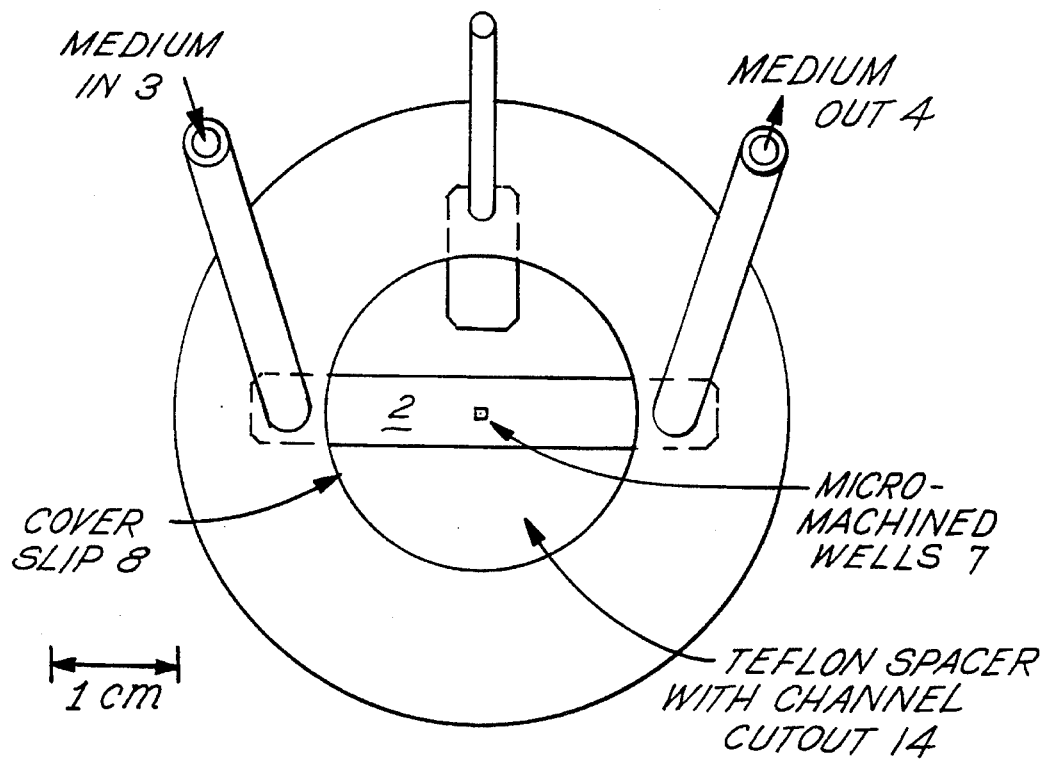
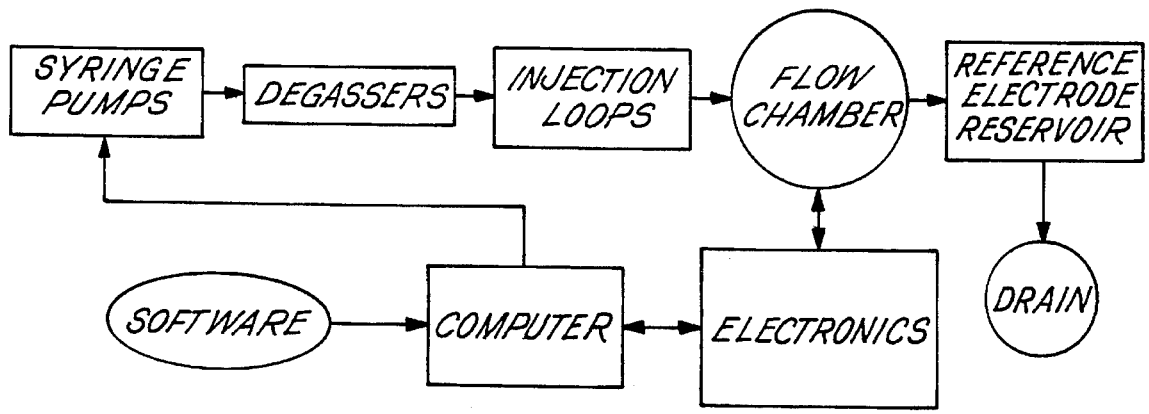

DEGASSER

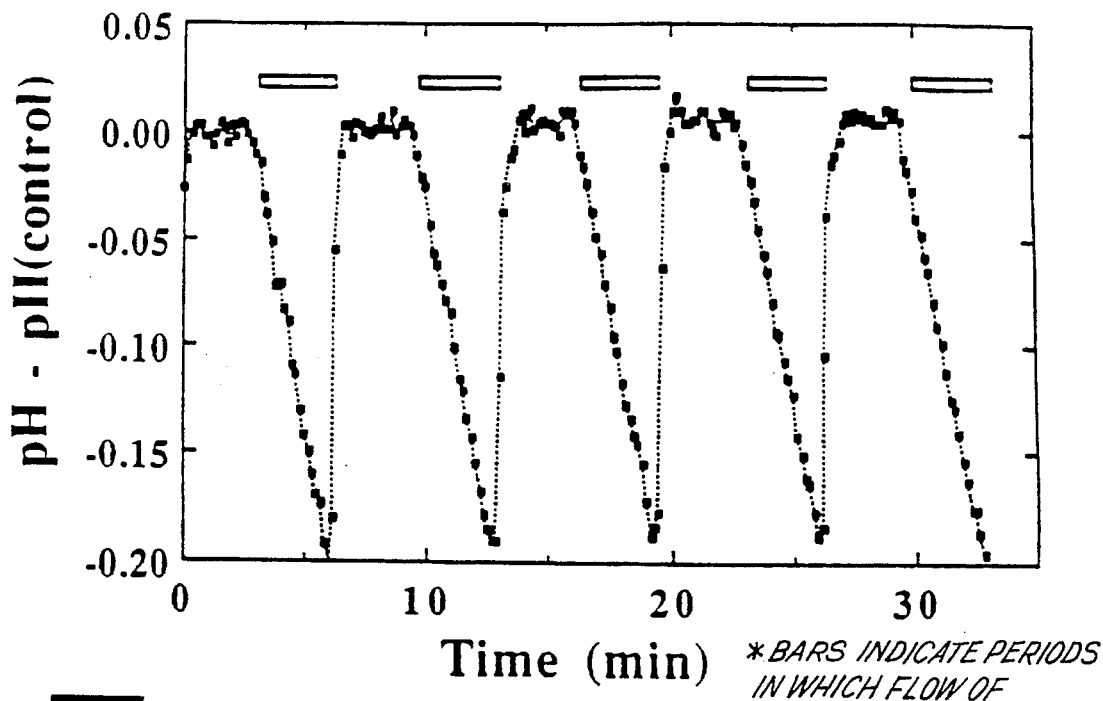
Fig. 10 Determination of Metabolic Rates
*BARS INDICATE PERIODS IN WHICH FLOW OF MEDIUM IS OFF
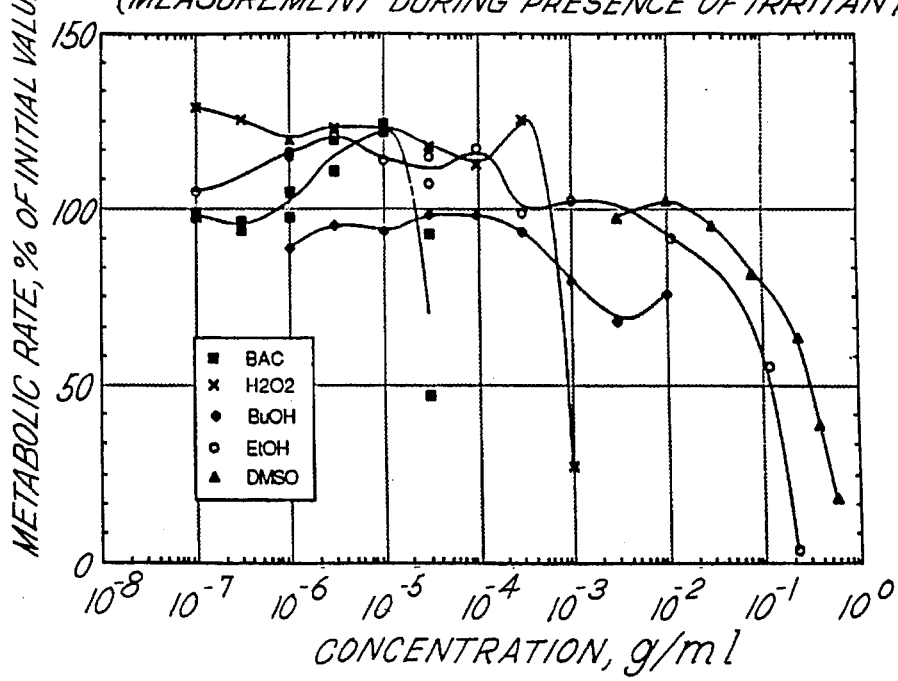
Fig. 11
EFFECTS OF IRRITANTS ON METABOLIC RATE OF KERATINOCYTES (MEASUREMENT DURING PRESENCE OF IRRITANT)

EFFECTS OF IRRITANTS ON METABOLIC RATE OF KERATINOCYTES (DEMONSTRATION OF RECOVERY)

Recovery from Exposure to Ethanol and DMSO

Effect of Valinomycin on L Cells

Effect of 100 μM Valinomycin on Fibroblastic (L) Cells

SLOT WELLS IN A STAINLESS STEEL FOIL

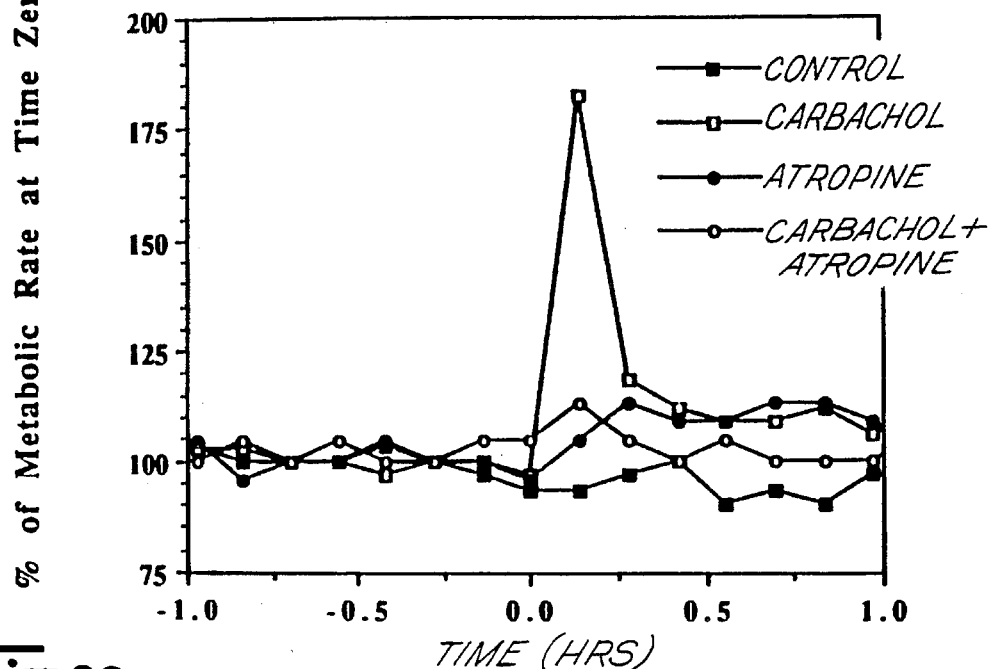
Fig. 28 Effect of 10 mM Carbachol, 10 µM Atropine, 10 mM Carbachol + 10 µM Atropine on MIC1 Cells Starved from FBS    6-20-89
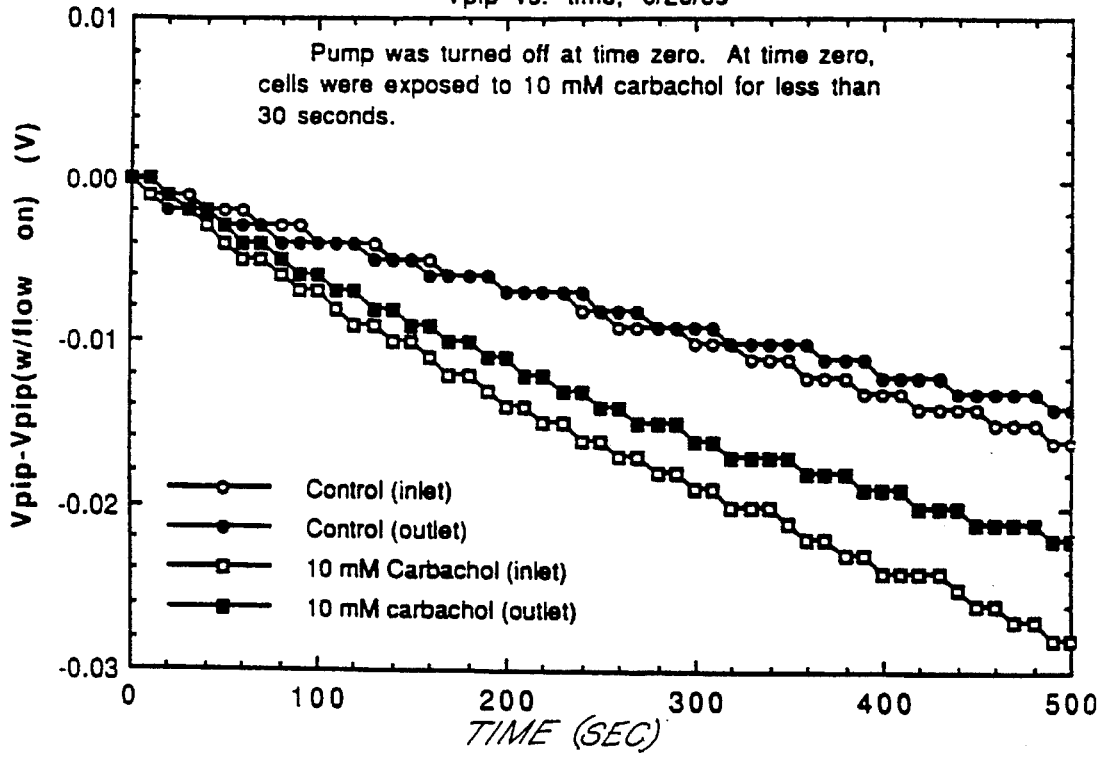
Fig. 29 Time Course of Carbachol Stimulation of MIC1 Cells
Vpip vs. time, 6/20/89

VSV Infection of L Cells- UV Inactivation

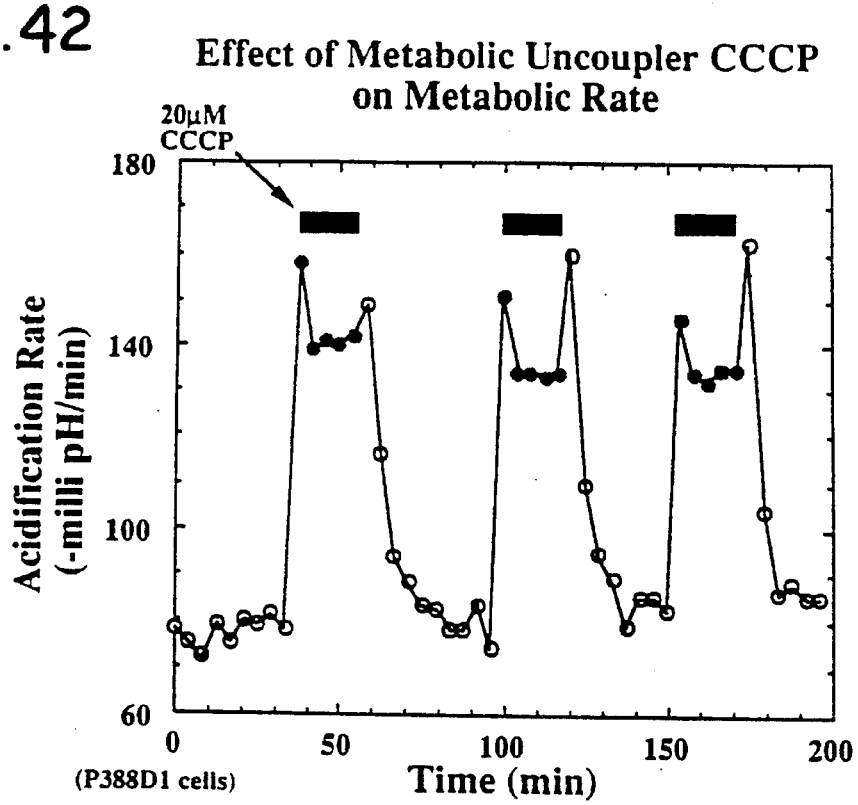
Fig. 42 Effect of Metabolic Uncoupler CCCP on Metabolic Rate
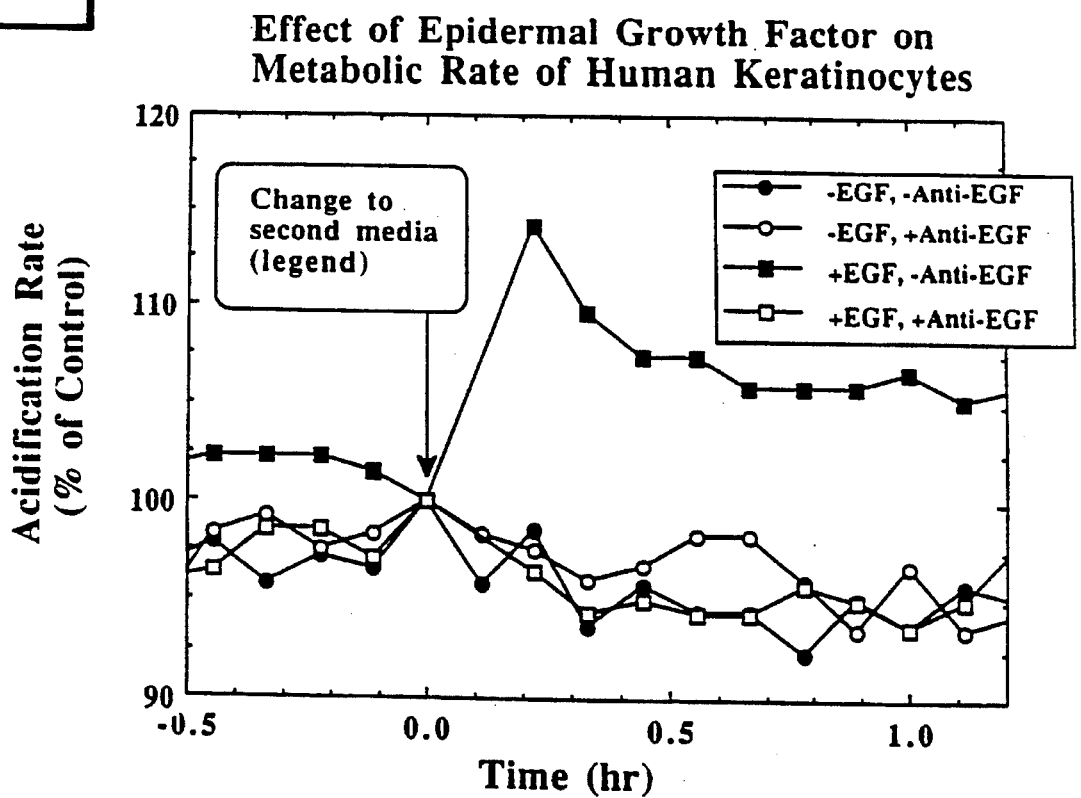
Fig. 43 Effect of Epidermal Growth Factor on Metabolic Rate of Human Keratinocytes

METHODS AND APPARATUS FOR DETECTING THE EFFECT OF CELL AFFECTING AGENTS ON LIVING CELLS

This application is a continuation of application Ser. No. 07/833,602 filed Feb. 11, 1992 (now abandoned), which is a continuation of Ser. No. 07/408,896 filed Sep. 18, 1989, (now abandoned) which is a continuation in part of application Ser. No. 07/260,521 filed Oct. 21, 1988, (now abandoned). Application Ser. No. 07/694,469 filed May 1, 1991 is a continuation in part of application Ser. No. 07/408,896 filed Sep. 18, 1989, which is a continuation in part of application Ser. No. 07/260,521 filed Oct. 21, 1988 (now abandoned). Application Ser. No. 07/708,121 filed May 29, 1991 is now U.S. Pat. No. 5,278,048 granted Jan. 11, 1994 and is a continuation of application Ser. No. 07/260,521 filed Oct. 21, 1988 (now abandoned).

BACKGROUND OF THE INVENTION

1. Field of the Invention

The present invention relates to methods for detecting the effects of cell affecting agents on living cells and to apparatus adapted to the practice of such methods. Solutions or suspensions of cell affecting agents are flowed over cells and the effects of these agents are measured.

2. Description of the Background of the Invention

Studies of the effect of various cell affecting agents on living cells have been reported in the literature. See, e.g., Meisner, H. and Tenny, K. (1977) "pH as an indicator of free fatty acid release from adipocytes," J. Lipid Research, 18:774–776; Nilsson, N. and Belfrage, P. (1979) "Continuous monitoring of free fatty acid release from adipocytes by pH-stat titration," J. Lipid Research 20:557–560; Reuss, L., Weinman, S. and Constantin, J. (1984) "$H^+$ and $HCO_3^-$ transport at the apical membrane of the gallbladder epithelium," pp. 85–96 of Forte, J., Warnock, D. and Rector, F. Jr. (eds.) *Hydrogen Ion Transport in Epithelia*, Wiley-Interscience; Zeuthen, T. and Machen, T. (1984) "$HCO_3^-/CO_2$ stimulates $NA^+/H^+$ and $Cl^-/HCO_3^-$ exchange in Necturus gallbladder," pp. 97, 108 (ibid.); Handler, J. S., Preston, A. S. and Steele, R. E. (1984) "Factors affecting the differentiation of epithelial transport and responsiveness to hormones," Federation Proceeding 43:2221–2224; and Simmons, N. L., Brown, C. D. A. and Rugg, E. L. (1984) "The action of epinephrine on Madin-Darby canine kidney cells," Federation Proceedings, 43:2225–2229. These references disclose the detection of changes in pH and other electrical potentials by the addition of cell affecting agents to cells disposed in a relatively large amount of medium, i.e., a bulk medium. A disadvantage of these techniques is that the pH and other electrical potential measurements are taken from the bulk medium and do not necessarily reflect the actual values immediately adjacent to the cellular membranes of the living cells. Also, the high ratio of bulk volume to cell volume inevitably dilutes the effects of the cells on the properties of the extracellular medium. Accordingly, sensitivity is lost or greatly reduced.

Photoresponsive sensors for measuring biochemical systems are disclosed in various patent documents owned by the assignee of the present invention. See. e.g., U.S. Pat. Nos. 4,591,550 (Hafeman et al.) and 4,704,353 (Humphries et al.); and European Patent Application No. 213,825 (Hafeman et al.). U.S. Pat. No. 4,519,890 discloses a flow pH chamber. These patent publications disclose the use of microorganisms to measure changes in the environment of the solution to be measured. There is no disclosure in these publications of cells in micro flow chambers used to measure of the effects of cell affecting agents. See, also, U.S. Pat. Nos. 4,737,464 (McConnell et al.) and 4,741,619 (Humphries et al.), which are likewise owned by the assignee of the present invention.

Various ways of using fluorescence to measure extracellular effects of living cells and analytes are disclosed in the literature. See. e.g., Briggs et al. (1985) "Fiber Optic Probe Cytometer" J. Immunological Methods, 81:73–81; Hafeman et al. (1984) "Superoxide Enhances Photo Bleaching During Cellular Immune Attack Against Fluorescent Lipid Monolayer Membranes" Biochemica Biophysica Acta 772:20–28; and U.S. Pat. Nos. 4,560,881 and 4,564,598.

SUMMARY OF THE INVENTION

It is an object of the present invention to provide methods for detecting the effects of cell affecting agents on living cells with greater accuracy and precision.

It is an additional object of the present invention to provide methods for detecting the effects of cell affecting agents on living cells that avoid the use of large volume, bulk media.

It is a specific object of the present invention to provide methods for detecting an effect of a cell affecting agent on living cells by: (a) providing living cells that are retained in a micro flow chamber adapted for continuous or intermittent flow of a solution or suspension containing the cell affecting agent in intimate contact with the cells so that the amount of cell affecting agent in contact with the cells may be controlled; (b) flowing a solution or suspension containing the cell affecting agent in intimate contact with the cells, thereby producing a cell mediated extracellular effect or change in pH, redox potential, cell surface potential or trans-cellular potential; and (c) measuring the effect of the cell affecting agent by a means for detecting pH, redox potential, cell surface potential or trans-cellular potential that is operably associated with the micro flow chamber.

It is a further object of the present invention to provide apparatus particularly adapted to practice the inventive methods.

In a preferred embodiment of the invention, the cells may be retained in the micro flow chamber by spontaneous or natural adhesion of the cells to the internal surface of the flow chamber or on a porous membrane or microcarrier contained in the flow chamber. Alternatively, the cells may be retained in the micro flow chamber by means of a binding agent that is biologically compatible with the cells. A preferred example of such a binding agent is agarose.

In another preferred embodiment of the present invention, the living cells may be retained in the micro flow chamber by providing the micro flow chamber with a surface having a plurality of wells or depressions that act to physically trap the cells on the surface of the micro chamber, preferably by gravitational sedimentation. These wells should be of a sufficient width and depth such that the cells remain in the micro flow chamber during ordinary flow rates. The cells may then be removed from the trapping wells by any appropriate means, including the use of high flow rates through the micro flow chamber that wash the cells out of the wells or by inversion of the chamber to dislodge the cells from the wells into the flow stream. In an alternative embodiment, the cells may be retained in the flow chamber by trapping them within a compartment of the flow chamber separated by a porous membrane.

Some features of the preferred geometry of the micro flow chamber used in the present invention are common to most applications of the device. Chief among these is the volume-to-surface ratio in the chamber, which controls the maximum concentration of adherent cells. The pH change per proton excreted by a cell is inversely proportional to the cell concentration and, therefore, to the volume-to-surface ratio. For the planar slab geometry of the chamber as described in FIGS. 1–4, this ratio is simply the chamber height, typically 100 μm.

The design tradeoff involving volume-to-surface ratio is principally one of sensitivity versus ease of fluid handling. With our present preferred apparatus, sensitivity becomes seriously degraded for ratios above approximately 200 μm. For thicknesses below approximately 50 μm we anticipate significant fluid-handling problems that might offset sensitivity gains. However, instrumental improvements, such as chambers micro-machined into the sensor surface, might allow an integration of fluidics and chamber on a much smaller scale, permitting the analysis of one or a few living cells at ratios of 10–50 μm.

The preferred volume of the micro flow chamber used in the present invention will depend to some extent on the intended application of the device. For example, if the number of cells available is a limitation, then submicroliter chamber volumes are preferred (e.g., 1 mm$^2$ surface area and 100 μm height, or 100 nL, containing about 10$^3$ cells). For other applications involving a larger number of cells, chamber volumes on the microliter or even milliliter scale can be envisioned (surface areas on the order of square centimeters, with about 10$^5$ cells/cm$^2$, but still maintaining approximately 100 μm chamber height). Thus, the preferred micro flow chamber has both a small total volume achievable in the chamber and/or a small height or volume-to-surface ratio.

The type of micro flow chamber that is preferably used in the inventive method is of the type disclosed in U.S. Pat. No. 4,591,550, the disclosure of which is incorporated herein by reference. An argon and/or helium/neon laser may be used as a source of energy in place of the light emitting diodes disclosed in U.S. Pat. No. 4,591,550. Alternatively, the micro flow chamber useful in the present invention may be of the type disclosed in pending U.S. patent application Ser. No. 876,925, filed Jun. 20, 1986, which is owned by the assignee of the present invention, the disclosure of which is incorporated herein by reference application Ser. No. 876, 925 is now U.S. Pat. No. 4,915,812 granted Apr. 10, 1990, Most preferably the micro flow chamber to be used in the present invention includes a silicon semiconductor electrode on or near which the living cells are retained. By means of this electrode, the various electrical effects caused by the cell affecting agent may be detected or measured. The micro flow chamber to be used in the present invention should preferably provide for both intermittent and continuous flow of solutions or suspensions, since either intermittent or continuous flow of solutions or suspensions may be used in practicing the present invention.

The present invention may be used in conjunction with either eukaryotic or prokaryotic cells, so long as the particular cells are capable of being retained in the micro flow chamber. Genetically transfected cells may also be used. In addition, a wide variety of cell affecting agents may be used, including irritants, drugs, toxins, other cells, receptor ligands, receptor agonists, immunological agents, viruses, pathogens, pyrogens, and hormones.

A wide variety of effects caused by the cell affecting agents may be detected or measured according to the present invention. Preferred effects include the pH, redox potential, and other electrical properties of the solution or suspension that flows in intimate contact with the living cells in the micro flow chamber, such as cell surface potential and transcellular potential. These effects may be measured or detected by a variety of conventional means. For example, pH can be detected by measuring the fluorescence or absorbance of a pH sensitive dye such as fluorescein or phenol red in the extracellular medium or fixed to a part of the chamber. In a similar manner other dyes can be used to detect redox potential.

The present invention also includes methods of identifying microbes, methods of screening for the activity of drugs, methods for detecting toxic substances and methods for detecting intercellular reactions. In these various methods, solutions or suspensions containing the desired cell affecting agent are flowed in intimate contact with the living cells retained in the micro flow chamber. The effect(s) of the cell affecting agent on the cells are then measured and provide the means by which bacteria may be identified, drugs screened, and toxins and intercellular reactions detected.

The present invention has several advantages over other methods of measuring metabolic activity, such as oximetry and microcalorimetry. Specifically, the present invention possesses rapid measurement time, enhanced sensitivity, noninvasiveness, generality and the potential for further miniaturization and integration.

Certain preferred embodiments of the present invention are discussed below in more detail in connection with the drawings and the detailed description of the preferred embodiments. These preferred embodiments do not limit the scope or nature of the present invention.

BRIEF DESCRIPTION OF THE DRAWINGS

FIGS. 1–3 represent schematic cross-sectional views of micro flow chambers useful in practicing the preferred inventive methods.

FIG. 4 represents a schematic top perspective view of a micro flow chamber useful in practicing the preferred inventive methods.

FIG. 5 represents a schematic diagram of apparatus useful in practicing the preferred inventive methods.

FIG. 10 represents a typical determination of cellular metabolic rates that may be made by use of the present invention.

FIGS. 11–23 represent the experimental results obtained in connection with Examples 1, 2, 4, 6, 9, 11 and 17.

FIGS. 26–46 represent the experimental results obtained in connection with Examples 19–23.

DESCRIPTION OF THE PREFERRED EMBODIMENTS

Referring to FIG. 5, the instrumental setup of the preferred embodiment preferably consists of one or more syringe drives or pumps, a degassing chamber, a selection valve or injection loop valve, a flow chamber, a reference electrode reservoir, and the associated electronics. required for the silicon semiconducting electrode sensor and data processing.

The syringe drives provide the solutions or suspensions (i.e., the medium) to the flow chambers at controlled flow rates. Both the flow rate and the on/off cycle of the syringe drives can be controlled by means of a computer during the data acquisition phase. Alternatively, other types of pumps, such as peristaltic pumps, can be used in place of the syringe drives.

Figure 6:
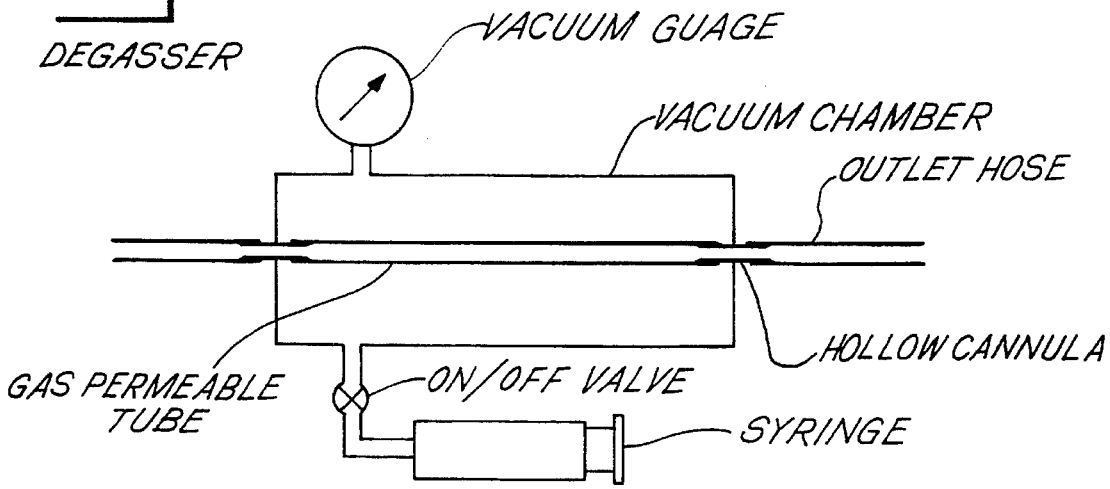
FIG. 6 represents a schematic diagram of a degasser useful in practicing the preferred inventive methods.

Referring to FIG. 6, the degassing chamber consists of the length of silicone rubber tubing through which the solutions or suspensions pass. The outside of the tubing is maintained in a reduced pressure air atmosphere (approximately ⅔ atmospheric pressure). A degassing chamber is preferred because the solutions or suspensions in the syringes and tubing are at room temperature and the flow chamber is commonly at 37° C. As the room temperature medium reaches the flow chamber it warms to 37° C. resulting in the formation of bubbles in the chamber. Bubbles in the flow chamber interfere with measurements in several ways. They can cause a high resistance path to the reference electrode resulting in an increase in noise in the photocurrent signal. They can also alter the aqueous volume in the chamber thus changing the buffer capacity of the chamber. For a given cellular metabolic rate, the rate of change of pH in the chamber will vary with the number and size of the bubbles. Bubbles form in the chamber and grow with time. When they reach a certain size they dislodge and are carried away in the flowing stream. This can create low frequency noise in the buffer capacity of the flow chamber.

The selection valve allows the user to direct the flow from one of two syringes into the flow chamber. An alternative is an injection loop valve. This allows the user to inject a bolus of solution or suspension into the flow stream without interrupting the flow. Typically when the injection loop valve is used, one syringe is loaded with medium and used to perfuse the stream by means of the injection loop. The volume of the agent solution or suspension and the time of exposure of the cells to the agent can be varied by varying the injection loop size and the flow rate of the perfusion stream.

Figure 1:
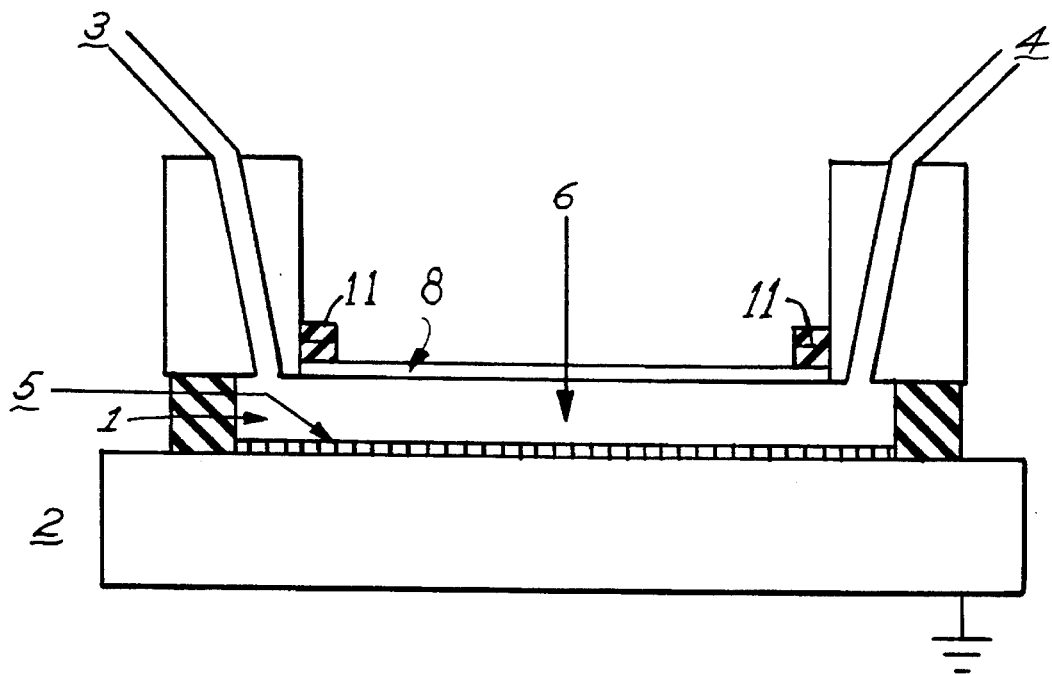
Figure 2:
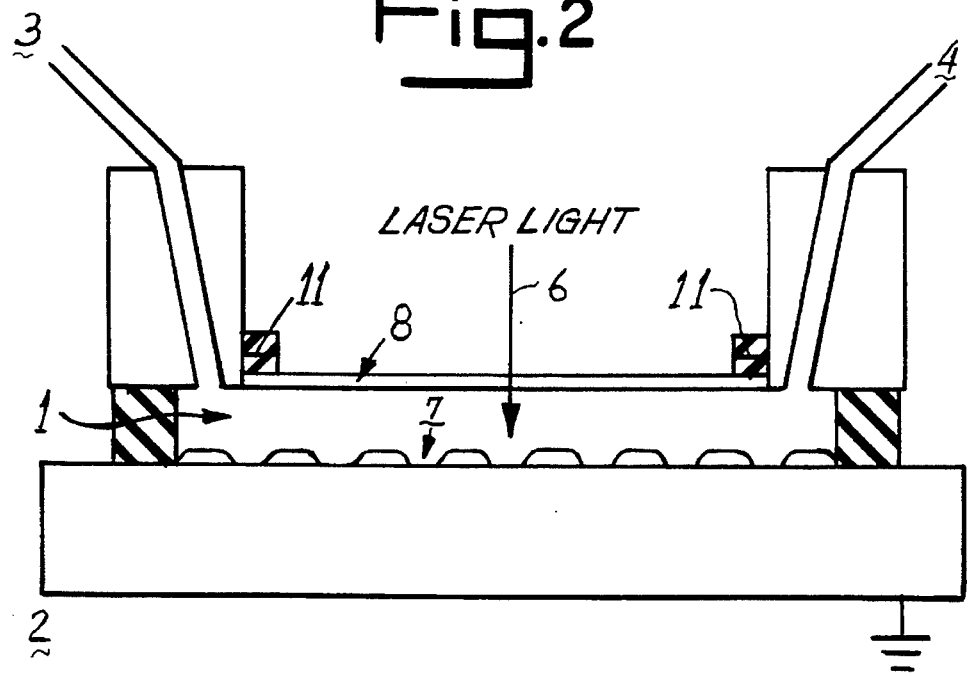

FIGS. 1–4 illustrate a preferred micro flow chamber 1 having a silicon sensor 2 with an inlet port 3 and an outlet port 4. In FIG. 1, cells 5 are adhered in a monolayer to the upper surface of silicon sensor and the response on the silicon sensor is modulated by laser light 6. Alternatively, the cell can be retained adjacent the silicon sensor by a permeable membrane. In operation, a solution containing a cell affecting agent enters through inlet port 3 and flows over cells 5 in the micro flow chamber 1. The solution exits outlet port 4 where the exiting solution is in electrical contact with a reference electrode. The local response on the upper surface of the silicon sensor 2 is modulated by laser light 6 and measured. FIG. 2 illustrates wells 7 that trap or retain therein cells during slow flow rates and from which the cells may be flushed out of the flow chamber during fast flow rates.

The flow chamber is preferably a thin channel bounded on the bottom by the silicon sensor 2, and on the top by an indium-tin-oxide (ITO) coated glass cover slip 8. Adherent cells may also be grown on the surface of the cover slip instead of the silicon semiconductor electrode. The spacing between the silicon sensor and the cover slip is approximately 100 μm. The spacing between the sensor 2 and the cover slip 8 may be achieved by means of a Teflon spacer 14 that has an appropriate channel cutout that forms the flow chamber. A controlling electrode 13, preferably a platinum wire, penetrates the plastic housing of the flow chamber to make electrical contact with the ITO controlling electrode. Electrical contact with the silicon sensor is made via the metal baseplate 9 of the flow chamber. Teflon inlet and outlet tubes, 3 and 4, penetrate the plastic housing and allow medium to flow through the flow chamber. The outlet tube 4 terminates in a reservoir that contains a Ag/AgCl reference electrode. Thus the outlet tube 4 acts as a salt bridge to allow measurement of the potential of solutions or suspensions in the flow chamber. The entire flow chamber is mounted on a hollow metal support that is maintained at constant temperature, typically 37° C., by a temperature controlled circulating water bath 10. The cover slip 8 is removable and may be maintained in operative position by means of removable silicon rubber gaskets 11 and retaining members 12.

Two different instruments may be preferably used for the purpose of illuminating the silicon sensor to generate a suitable photoresponse: a laser instrument and a light emitting diode (LED) instrument.

In the laser instrument, the flow chamber is mounted on a light microscope stage. The beam from a 150mW argon ion laser is directed through a 10 kHz mechanical chopper and into a beam expander that generates a beam approximately 2.5 cm in diameter. The beam then passes through a polarizing filter (variable attenuator) and is directed by mirrors through a quadruple knife edge adjustable aperture into the barrel of the microscope. Alternatively, in one version of the apparatus, the chamber is mounted on a microscope stage and the beam from a 10 mW HeNe laser is projected through an epi-illumination system onto the sensor. In these configurations, one can see the cells in the flow chamber through the microscope and can direct a square or rectangular probe beam of any desired size to any region of the silicon surface in the flow chamber. This is particularly useful when nonconfluent cell cultures are used. It allows one to direct the probe beam to regions of greatest cell density. In addition one can control for instrumental drift by directing the beam to regions where no cells are visible.

In the LED instrument, two flow chambers are mounted side by side on a temperature controlled plate. For illumination, four fiber optic light guides for each chamber penetrate the temperature controlled plate to illuminate the silicon sensor from underneath (the side opposite the surface in contact with the medium). The four fibers are aligned so as to have one near the inlet tube, one near the outlet tube, and two equally spaced between the inlet and the outlet. This instrument is preferably used with cells that grow to a reasonably consistent and uniform density. However, it still gives some latitude in picking regions of greatest cell density. One end of the optical fibers butts up against the silicon sensor and the other end is coupled to an infrared LED. Each fiber is 1.5 mm in diameter. Data can be collected from eight sites (four for each of the two chambers) simultaneously every four seconds.

There may be three primary electrical connections to the chamber: (1) a controlling electrode connected to the indium-tin oxide coating on the cover slip via a thin platinum ribbon or wire; (2) a Ag/AgCl reference electrode in an external well that measures the potential of solution in the flow chamber via a salt bridge comprising the chamber's outlet tube; and (3) an ohmic connection to the base of the silicon chip. A personal computer with a custom circuit board may handle the acquisition, analysis, and display of data in ways that are well known in that art.

Figure 9:
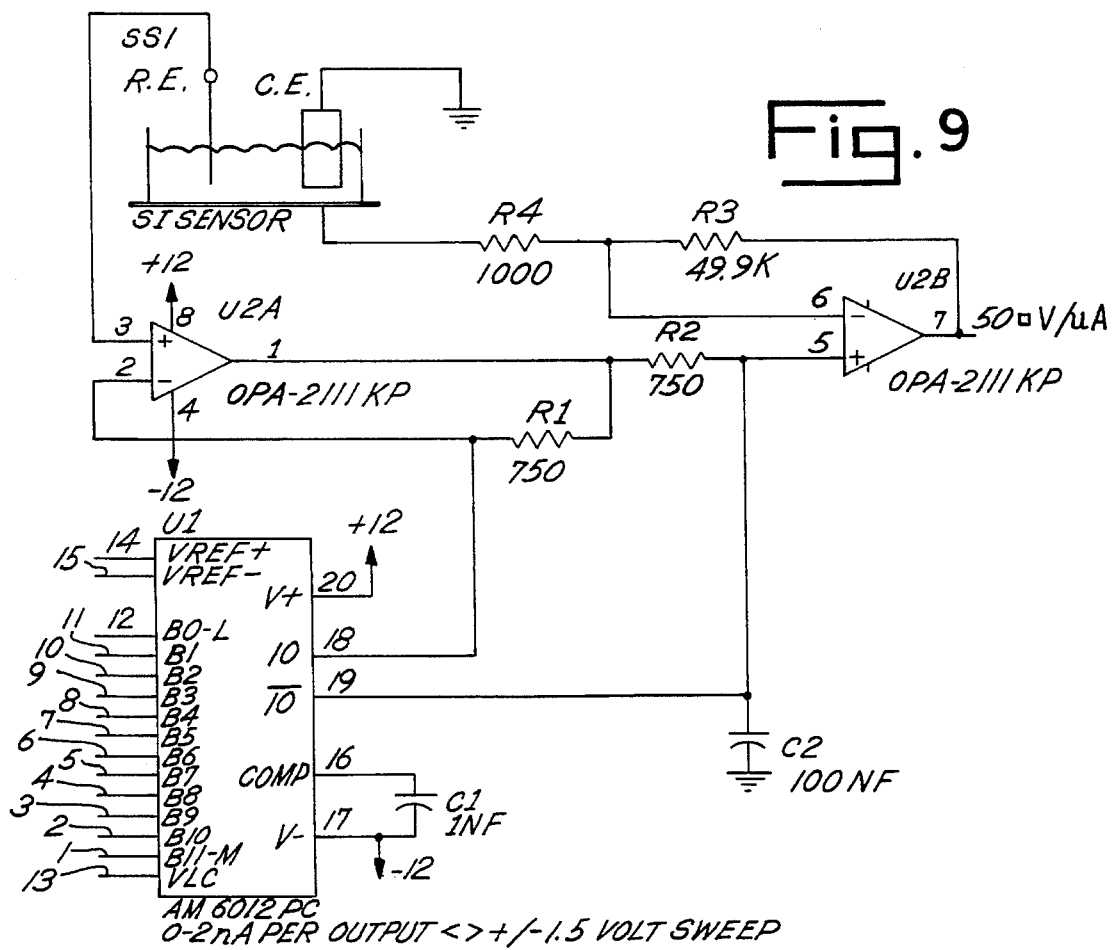
FIG. 9 represents a diagram of a circuit useful in the present invention.

A preferred circuit for use in the present invention is disclosed in FIG. 9. The sensor electrode system is shown comprising a silicon sensor, a reference electrode (R. E.) and a controlling electrode (C. E.). The controlling electrode maintains the solution at an arbitrary potential with respect to ground via a low impedance contact to ground. The arbitrary potential is defined by the surface potential at the electrode/solution interface and the various contact potentials between the electrode material and ground. The reference electrode is of the salt bridge type, and thus measures the potential of solution independent of solution composition. The purpose of the electronic circuit is twofold. First, it allows for varying the potential from the solution to the electrical contact to the silicon. Second, it converts a photogenerated alternating current to an alternating voltage (the output signal). U2A is configured as a conventional voltage follower whereby the reference electrode potential is buffered. U1 is a digitally controlled bipolar current source. A connection between pins 18 and 19 forms a current loop. The sign and magnitude of the current in this loop is controlled by the digital word applied to pins 1 through 13. The potential on pins 18 and 19 floats with respect to ground. As configured in the circuit, the combination of U1 and U2A allows the voltage at pin 5 of U2B to be offset from the voltage at pin 3 of U2A. The sign and magnitude of this voltage offset are determined by the digital word applied to U1, and the values of R1 and R2. U2B is used both as a voltage follower to apply a known offset voltage through R3 and R4 to the silicon, and as a current to voltage converter to convert the alternating photocurrent to an alternating voltage at pin 7. The signal gain of U2B is determined by R3. R4 is used to match the impedance of the circuit to that of the sensor. The voltage from silicon to solution is swept by applying a series of incrementally increasing words to U1. The signal amplitude (alternating photocurrent) is read out at U2B pin 7 as a function of potential applied from solution to silicon.

Figure 7:
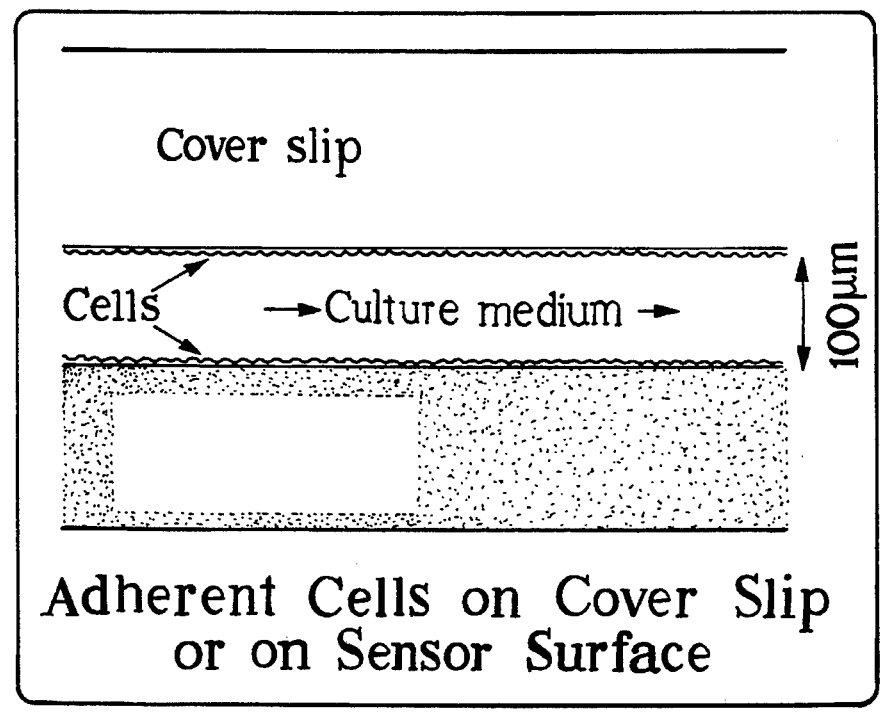
FIG. 7 represents a schematic side view of adherent cells located in a micro flow chamber.

Living cells may be adhered to the chamber in a variety of ways. As shown in FIG. 7, naturally adherent cells may be grown either on the surface of the silicon sensor or the cover slip in an incubator or both. The flow chamber is assembled while keeping the cells moist. Flow is established quickly to keep the cells from over acidifying the medium or consuming all of the oxygen in the chamber. For non-adherent cells, the cells may be mixed with an agarose solution at 37° C. and plated onto the surface of the silicon sensor or cover slip in an approximately 50 μm thick layer in a humid atmosphere. The silicon sensor is then refrigerated for about 15 min. to solidify the agarose. The flow chamber is then assembled and used.

Collagen and gelatin may also be used in conjunction with or in place of agarose. Fibronectin, chondronectin, laminin or other similar substances may optionally be used in adhering the living cells to the surface of the micro flow chamber. Alternatively, the living cells may be dispersed on or in biologically compatible microcarrier beads.

In another embodiment, cells may be grown on or in a porous membrane. This membrane may be inserted into the flow chamber between the controlling electrode and the sensor surface so that culture medium flows along at least one side of the membrane. Some cells, such as epithelial cells, form a monolayer with differential apical and basolateral surfaces. In such cases the properties of both sides of the cell sheet can be studied separately by controlling which side of the membrane is closer to the sensor surface.

The generally preferred inventive method may be practiced as follows. The chamber is assembled with living cells retained therein and attached to the fluidics in the instrument. Flow (typically 100 μL/min) of a low buffer capacity solution or suspension is established and the signal from the sensor is allowed to stabilize. Normal cell-culture medium may be used, including serum if desired, except that bicarbonate and buffers such as HEPES should be excluded. Some drift is seen initially due to warming of the chamber and equilibration of the chamber with the new medium. Once stable, flow in the chamber is halted and the silicon sensor signal is monitored. A decrease in potential reflects the decrease of pH in the chamber due to cellular metabolism. The rate or slope of pH decrease is a measure of the metabolic rate of the cells. The pH is allowed to drop far enough to obtain enough data points to accurately determine the slope of the line (within a few percent error). Typically this reflects a pH drop of approximately 0.1 to 0.5 pH units and requires approximately 1 to 4 minutes. Flow is then restarted and the pH returns to the initial value. This sequence is repeated until reproducible slopes are obtained. A typical determination of metabolic rate is shown in FIG. 10.

In another preferred embodiment, medium is flowed continuously over the cells and the potential is measured at a plurality of sites. If one site is located upstream of the direction of flow from another and there are intervening cells, there will be a pH difference between the two sites with the upstream site being less acidic. This pH difference is due to the metabolic action of the cells on the medium as it traverses the space between the sites. The magnitude of this pH difference, as detected by the silicon semiconductor electrode, is a measure of the metabolic rate of the cells located between the two sites.

For testing cell affecting agents, two strategies may be advantageously employed. In one approach, two syringe drives are used. First metabolic rates are determined as described above with a control medium. Then the syringe drive with the control medium is turned off and a syringe drive with the same medium plus the cell affecting agent is turned on. An appropriate selection valve directs the flow from either syringe drive to the flow chamber. Metabolic rate measurements are then taken in the presence of the cell affecting agent. The flow can be switched back to the control medium to observe recovery of the cells from the effect of the cell affecting agent.

In a second approach, an injection loop valve is used. Metabolic rates are determined as described above. Once they are stable, the cell affecting agent is introduced into the injection loop, and the valve is turned such that the cell affecting agent is introduced into the flowing medium stream. Metabolic rates can then be measured in the presence of the cell affecting agent and can be followed after the agent is washed out of the chamber. This technique is particularly suited for testing for cell responses to brief exposure to cell affecting agents.

If the living cells to be used are not naturally or spontaneously adherent to a surface of the micro flow chamber, means of retaining the cells in the chamber must be used. Three desirable ways of achieving this result are the provision of wells capable of physically retaining the cells, the provision of a compartment in the micro flow chamber that retains the cells by means of a membrane that is porous or permeable to the cell affecting agent in the solution or suspension, and the use of biologically compatible adhering agents.

Figure 8:
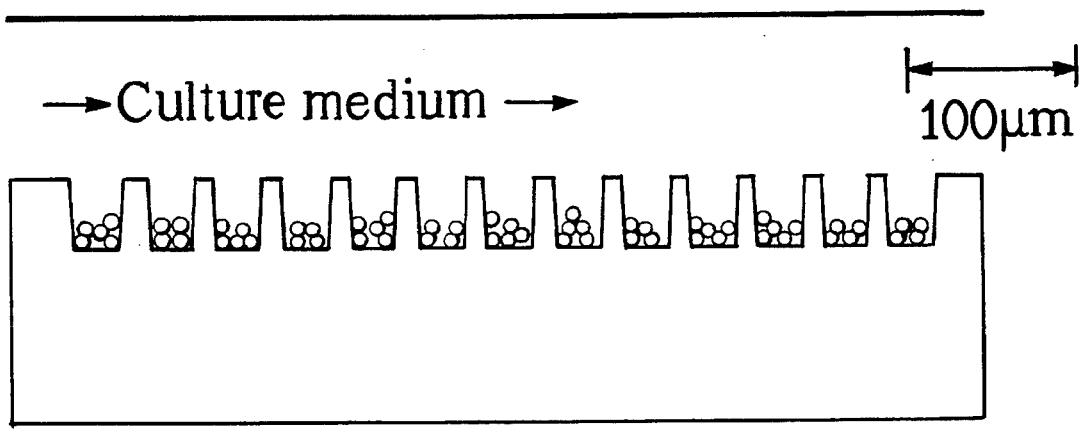
FIG. 8 represents a schematic side view of cells retained in wells in a micro flow chamber.

In the embodiment employing wells, as shown in FIG. 8, the floor of the flow chamber contains the wells. The wells may be circular in crosssection or may be trenches aligned perpendicularly to the direction of flow. The smallest horizontal dimension of the wells should be at least one cell diameter, preferably no more than several cell diameters. The depth of the wells can be several cell diameters. Wells 50 µm in diameter and 50 µm deep are acceptable. The use of wells to retain the cells is well adapted for the analysis of multiple batches of cells by employing the following cycle of operations.

The first step is loading cells into the wells. At sufficiently slow flow rates cells will sediment into the wells and remain trapped therein.

Next, the cellular behavior is analyzed. The composition of the medium flowing over the wells can be altered according to the desired analytical protocol. Compounds from the medium reach the cells in the wells by a combination of diffusion and convection.

Finally, the cells are flushed out of the wells. At sufficiently high fluid flow rates, vortex behavior in the wells becomes strong enough to cause the cells to be resuspended and to be swept out of the wells and out of the chamber. This clears the chamber for the next loading of fresh cells.

There are at least two important advantages to the well method. First the method of immobilization is nonperturbing. Second, the system is easily automated to provide repetitive analyses of fresh batches of cells in the same micro flow chamber.

In the embodiment employing biologically compatible adhering agents, non-adherent cells may be retained in the flow chamber in a very thin (preferably 50 µm thick) layer of agarose covering the floor of a flow chamber having a total depth 100 µm and surface area about one cm$^2$. Medium flows through the 50 µm gap remaining between the ceiling of the chamber and the top of the agarose layer.

The thinness of the agarose layer permits rapid and virtually unimpeded access of the immobilized cells to the components of the medium flowing over the agarose. Transport between the cells and the flowing medium is diffusive. Diffusion times on the order of one to ten seconds are to be expected for most solutes.

The cell retaining wells are preferably formed on the surface of the silicon semiconductor electrode or sensor. They may be formed as indentations in the surface of the electrode or by application of a grid structure on top of the upper surface of the electrode. The grid structure is preferably formed of an electrically compatible semiconducting material, i.e. silicon, but may be formed of electrically neutral materials. For example, a nylon mesh comprised of 25 µm diameter threads woven to produce 25 µm square holes may be glued to the surface of the silicon semiconductor electrode with a spray adhesive. The adhesive forms widely dispersed fine droplets on the silicon electrode and therefore only attaches the nylon mesh to the surface at a few discrete points. In this manner, the nylon mesh may be attached to the silicon electrode without totally coating the silicon electrode with adhesive and thereby destroying the photoresponse of the electrode.

With adherent cells, unpatterned silicon surfaces may be fabricated by first growing a thin (30 nm) thermal SiO$_2$ film, followed by a deposition of 100 nm of Si$_3$N$_4$ by low-pressure chemical vapor deposition. The first step in the fabrication of the micromachined sensor for use with non-adherent cells is to grow a 1 µm thick SiO$_2$ layer by steam oxidation, followed by photolithographic patterning to form openings where the cavities will be located. The cavities are then anisotropically etched in an SF$_6$/C$_2$ClF$_5$ plasma, producing cavities with sidewalls at an angle of >85° from the horizontal. The final steps in the process are the growth of the thin oxide and the nitride deposition, as in the unpatterned case. The micromachined sensors thus have a thick oxide layer on the areas between cavities, effectively deactivating the sensing capability there. The active sensing surfaces are only the inside walls and floor of the cavities, improving the signal-to-noise performance of this version of the device.

The device detects the surface potential at the interface between the electrolyte and the Si$_3$N$_4$ insulator. The presence of protonarable silanol and amine groups on this surface ensures that this potential depends on pH in a Nerstian fashion. The pH is detected only at portions of the interface corresponding to illuminated regions of silicon.

The present invention may be used with a wide variety of prokaryotic and/or eukaryotic cells. Examples of such cells include human keratinocytes, murine L fibroblastic cells, canine MDCK epithelial cells, hamster BHK fibroblastic cells, murine CTLL lymphocyte cells, tumor cells and bacteria. In general, any living cells, including transfected cells, that can be successfully retained within a micro flow chamber may be used.

The present invention may be used with a wide variety of cell affecting agents. Examples of such cell affecting agents include irritants such as benzalkonium chloride, propylene glycol, methanol, acetone, Na dodecyl sulfate, hydrogen peroxide, 1-butanol, ethanol, and DMSO; drugs such as valinomycin, doxorubicin, vincristine, ribavirin, amiloride and theophylline; hormones such at $T_3$ and $T_4$, epinephrine and vasopressin; toxins such as cyanide, carbonylcyanide chlorophenylhydiazone, endotoxins and bacterial lipopolysaccharides; immunological agents such as interleukin-2, epidermal growth factor and monoclonal antibodies; receptor agonists such as isoproterenol, carbachol, prostaglandin $E_1$ and atropine; and various other types of cell affecting agents such as phorbol myristate acetate, magnesium chloride, other cells, receptor ligands, viruses, pathogens and pyrogens. This invention also encompasses the measurement of the effects of water immersible cell affecting agents such as particulate matter, greases, and oils on cells. These substances can be delivered to the vicinity of cells by aqueous or non-aqueous fluids.

The present invention includes methods for identifying microbes such as yeast, bacteria, and fungi. In these inventive methods, the bacteria to be identified are trapped or retained within the flow chamber. A predetermined set of solutions and/or suspensions are then sequentially flowed through the micro flow chamber such that they come in contact with the bacteria. Each of these solutions and/or suspensions contains an ingredient that produces a particular response from known bacterium. When the solution and/or suspension containing this ingredient are contacted with bacteria to be identified, the bacteria in the micro flow chamber either produce a characteristic response or produce no response. The response or absence of response is then measured by means of the silicon semiconducting electrode. The response or lack of response to the predetermined set of solutions and/or suspensions may then be compared to the response of known bacteria to the predetermined set of solutions and/or suspensions in order to positively identify the bacteria being tested.

The present invention also includes methods for screening for the activity of a drug. In these inventive methods, living cells that are responsive to the drug to be screened for are trapped or retained within the micro flow chamber. A solution or suspension suspected of containing the drug may then be flowed into intimate contact with these living cells. Upon contact with the living cells, the solution or suspension suspected of containing the drug will produce a response in the living cells or produce no response at all. This effect or lack of effect of the drug on the living cells is then measured by means of the silicon semiconductor electrode. Such drugs may include antibiotics active against microbial cells. The presence or absence of the expected effect may be used as a means for screening solutions or suspensions for the presence of a drug.

The present invention also includes methods for detecting toxic substances. In these inventive methods, living cells that are responsive to the toxic substance being tested are trapped or retained within the micro flow chamber. The solution or suspension suspected of containing the toxic substance is then flowed into intimate contact with the living cells. Any reaction or lack of reaction of the living cells to the solution or suspension is measured, thereby providing a means for detecting the presence of the suspected toxic substance.

The present invention also includes methods for detecting intercellular reactions. In these inventive methods, two sets of living cells are provided within the micro flow chamber. A solution or suspension containing an agent that affects the first set of cells is flowed through the micro flow chamber. This causes the first set of cells to elaborate a second cell affecting agent. The second cell affecting agent in turn causes a response in the second set of living cells. This response is measured by means of the silicon semiconductor electrode. In this way, the intercellular reactions of different sets of living cells may be measured. The first and second sets of cells may be of the same type or may be of different types.

EXAMPLE 1

Keratinocytes are the cells that generate the epidermis. Studies have been done to assess the response of these cells to irritants that might contact the skin in the workplace, in cosmetics, and elsewhere. For example, Shopsis and Eng (Shopsis, C. and Eng, B. (1988) in *Alternative Methods In Toxicology*, Vol. 6)) determined the concentration of an irritant necessary to inhibit protein synthesis by 50% in a 48-hour incubation of keratinocytes with the irritant. The ranking of a series of detergent irritants by this method agreed well with the rankings obtained by the standard in vivo Draize test of ocular irritancy (Draize, J., Woodard, G. and Clavery, H. (1944) *J. Pharmacol. Exp. Ther.*, 82:377–390).

Normal human keratinocytes were obtained from Clonetics, Inc. (San Diego, Calif.) and cultured according to the vendor's instructions. The cells were grown to between 50% and 100% confluency on the conductive indium-tin-oxide surfaces of the glass cover slips used in the cell flow chamber. The irritants tested were benzalkonium chloride (BAC; a cationic detergent), hydrogen peroxide ($H_2O_2$), 1-butanol (BuOH), ethanol (EtOH), dimethyl sulfoxide (DMSO), propylene glycol, methanol, acetone and sodium dodecyl sulfate.

The cover slip was assembled in the chamber, and flow of medium was initiated. Clonetics provided a low-buffered modification of their Keratinocyte Growth Medium for this purpose; it contained neither bicarbonate nor HEPES buffer.

The flow of medium was controlled by a computer-interfaced syringe pump. Flow was alternately on for 200 sec and off for 200 sec. During the flow-off time, the metabolic rate was determined as the slope of the trace of sensor potential (i.e., pH) vs. time.

Irritants were injected via a 300 µl sample injection loop (of the type used in liquid chromatography) at the beginning of a flow-on period.

The flow rates, on the order of 100 µl/min, were adjusted so that the irritant was present in the cell chamber during the next flow-off period but had been cleared by the second flow-off period. Typically, samples were injected at 800-sec intervals, allowing two determinations of metabolic rates for each injection (one with the irritant present, one after it had cleared).

After a stable metabolic rate had been established in the absence of irritants, irritants were injected as described above, working from low to high concentration. Often there were two injections of each concentration. An entire experiment took three to five hours, though a response to each dose of irritant was obtained 400 sec after sample injection. As a control, the metabolic rates of one set of keratinocytes that were administered no irritants were measured over several hours.

The metabolic rate of the control cells remained stable throughout the experiment, with a coefficient of variation of about 6%. FIG. 11 shows the results for five of the irritants, plotted as metabolic rate vs. the logarithm of irritant concentration. Metabolic rate is expressed as a percent of the value prior to the introduction of irritant. When two successive doses were administered at the same concentration, both sets of data are presented. The large differences in such points at, e.g., 30 µg/ml BAC, represents a real decrease of cellular metabolic rate between the two administrations, not mere scatter in the data. The actual concentration of $H_2O_2$ may have been less than indicated, due to redox reactions with compounds in the medium as well as disproportionation reactions. For some irritants the metabolic rate rose above the control level for irritant concentrations just below those that were sufficient to inhibit metabolism.

Figure 12:
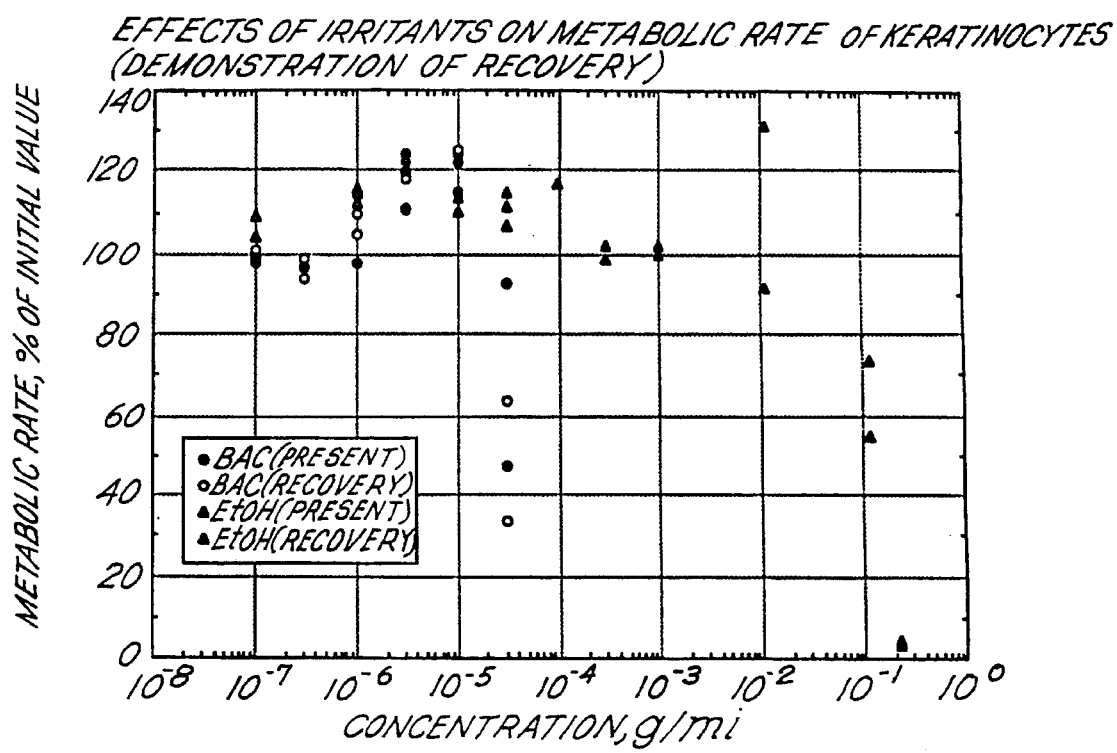
Figure 13:
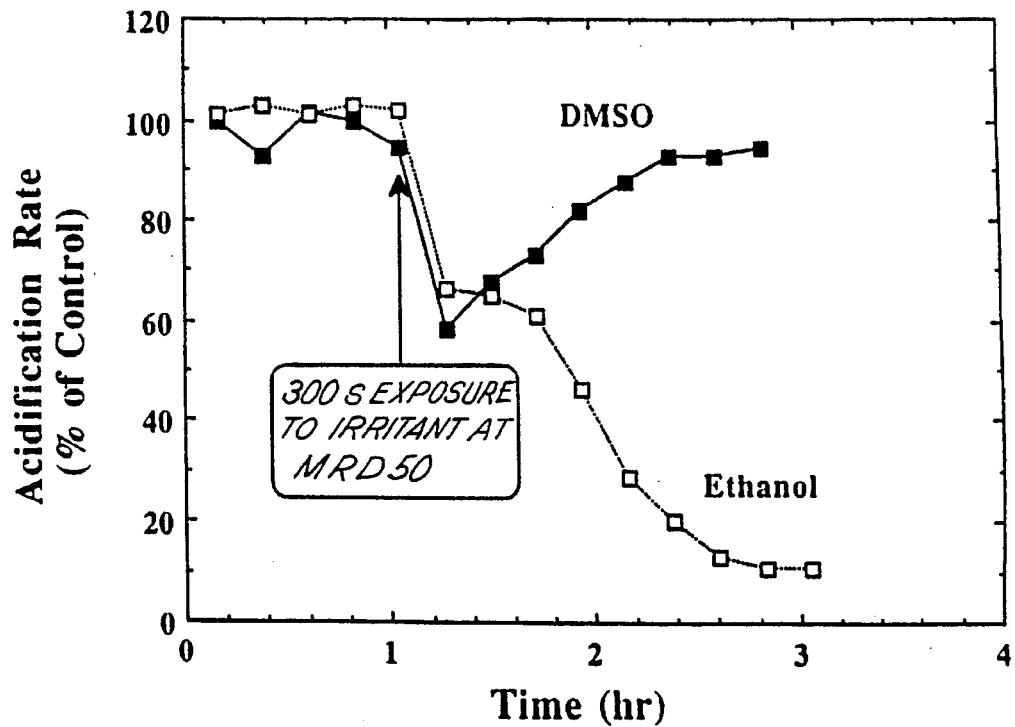

FIG. 12 is a comparison of measurements taken during the presence of the irritant and after washout. The closed symbols represent rates obtained during the presence of the irritants on the cells; the open symbols correspond to the rates obtained immediately after the irritants were washed out. For one irritant, BAC, no recovery was obtained; in fact, metabolism continued to decrease with each measurement after the higher doses. For EtOH, there was substantial recovery. In a separate test, recover from DMSO but not from ethanol was shown (see FIG. 13).

The irritant strength of these compounds has been given the following classification by in vivo tests such as the Draize test (see, e.g., Dubin, H. and Ghodgaonkar, R. (1987) *In vitro Toxicology*, 1:233–240):

TABLE I

| Irritant | In-Vivo Irritancy | $-\log_{10}$ (MRD$_{50}$) |
| --- | --- | --- |
| Dimethyl sulfoxide | Mild | 0.1 |
| Propylene glycol | Mild | 0.5 |
| Methanol | Moderate–mild | 0.7 |
| Ethanol | Moderate–mild | 0.8 |
| Acetone | Moderate–mild | 0.9 |

TABLE I-continued

| Irritant | In-Vivo Irritancy | $-\log_{10} (MRD_{50})$ |
|---|---|---|
| n-Butanol | Moderate | 1.7 |
| Na dodecyl sulfate | Severe–moderate | 3.9 |
| Benzalkonium Cl | Severe | 4.1 |

The ranking of the concentrations necessary to depress metabolism, shown as $-\log_{10} (MRD_{50})$ above, in this example agrees well with that obtained by the in vivo tests.

The inventive method allows flexible control of both the duration and concentration of exposure of the cells to the irritants. Furthermore, it permits one to monitor the effects of these agents on cell metabolism both while the irritants contact the cell and then later, after the irritants have been washed out. Thus, the kinetics of recovery from the insult can be determined along with the main inhibition analysis.

This example demonstrates the feasibility of performing rapid in vitro toxicological assays with the inventive method. Responses to acute exposure have been obtained in a few minutes. Further automation and exploitation of parallelism would bring the time for an entire experiment down to that amount of time. This is a significant advantage in speed and capability over existing in vitro methods.

EXAMPLE 2

Valinomycin is a peptide antibiotic that exerts its effects by inserting itself into cell membranes and rendering them permeable to potassium ions. It is commonly used in research applications where membrane permeability to ions is important. Within no more than a few minutes after being exposed to 100 μM valinomycin, the metabolic rate of L cells rises significantly; at its peak it may be more than double the initial rate. Following the peak, the rate drops.

Figure 14:
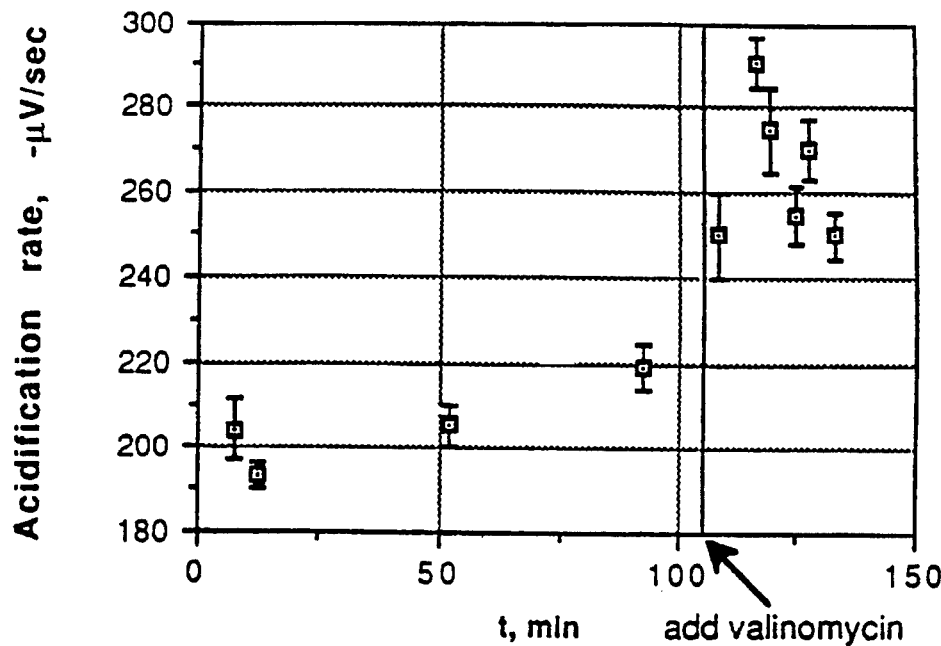
Figure 15:
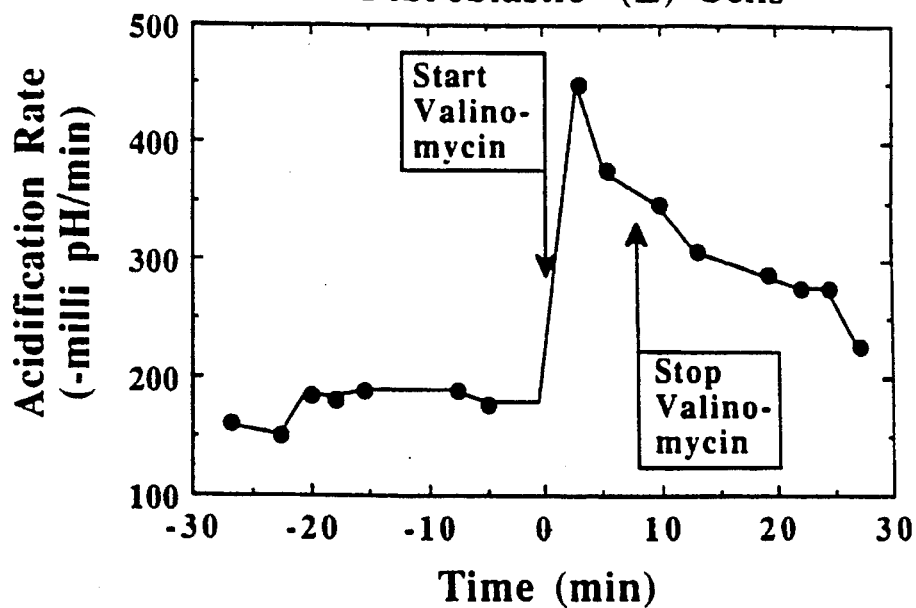

FIG. 14 shows the response to a brief pulse of valinomycin according to the inventive method (75 μl injected into the medium stream; flow rates about 100 μL/min). Similar results are shown in FIG. 15. In other experiments (graph not shown) the same concentration of valinomycin was administered continuously for 8 minutes and the metabolic activity rose to a peak of approximately 2.4 times the initial value four minutes after the start of exposure. It returned approximately to the initial value within 20 minutes of the removal of the antibiotic. This biphasic response may be an initial expenditure of cellular metabolic energy to attempt to maintain electrolyte homeostasis, followed by the toxic effects of the cells' failure to accomplish this.

EXAMPLE 3

L cells were Brown to confluence on the silicon sensor surface of the flow chamber and alternately perfused with normal medium and medium containing 10 nM each of the thyroid hormones tritodothyronine ($T_3$) and thyroxine ($T_4$). In one experiment when the hormone was first introduced, the metabolic rate increased by 12% and decreased to 9% below the initial level when the hormone was withdrawn. This is in accordance with the expectation that the hormone increases the overall metabolic activity of the cells.

EXAMPLE 4

Phorbol myristate acetate (PMA) is one of the tumor-promoting phorbol esters. Among its effects are an increase in cellular cyclic AMP levels and the deacylation of phospholipids to produce arachidonic acid; it is known to interact with protein kinase C (see, e.g., Daniel, L. (1985) *Phosphatidylinositol Turnover in MDCK Cells, in Inositol and Phospoinositides: Metabolism and Regulation*, (eds.) Bleasdale, J., Eichberg, J., and Hauser, G. Humana Press). MDCK cells (Madin-Darby Canine Kidney) are an epithelial line that retain many of the functional characteristics of kidney tubule epithelia. One characteristic is that a confluent monolayer of these cells forms a relatively tight seal, both electrically and to the diffusion of ions, separating the aqueous regions on the two sides of the cells.

The sealing property of the MDCK cells implies that when the cells are grown on the surface of the silicon sensor, the signal does not necessarily represent merely the pH of the fluid in the flow chamber. It contains information on the pH of the small aqueous compartment between the cells and the sensor, and it contains information about trans-cellular potentials, which are essentially batteries in series with the electronic circuit of the sensor. In cells that do not form a tight seal, the subcelluar pH is essentially identical to the flow chamber fluid pH and any trans-cellular potentials are shorted out as far as the sensor is concerned.

Figure 16:
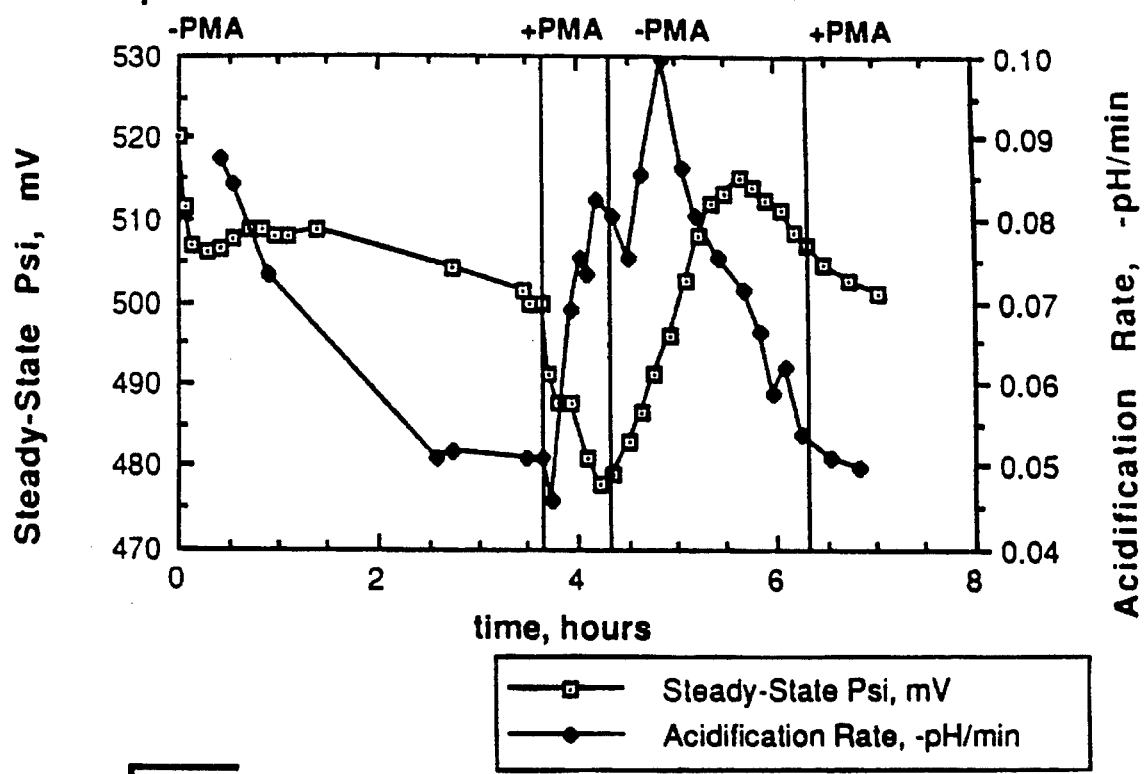

FIG. 16 shows the strong and rapid response that was observed when medium containing 10 ng/ml PMA was introduced into the system. The steadystate potential reported by the sensor (with fluid flow on) decreased gradually from the time the sensor was activated until the PMA was introduced. At that time it dropped quickly to a minimum about forty minutes later when the PMA was removed, then increased and finally returned to a value near its initial one by the end of the experiment. This signal is a composite of the trans-cellular potential and the sub-cellular pH (changes in the latter corresponding to 59 mV per pH unit).

The introduction of PMA coincided with a sharp rise in the metabolic rate of the cells, more than a doubling at the peak near an hour later. Similar experiments with MDCK cells grown on the cover-slip surface of the chamber give no information about trans-cellular potentials but also indicate an increase in metabolic rate upon the addition of PMA (data not shown).

The metabolic rates determined from cells grown on the sensor surface are more sensitive to the treatment of the cells and generally less stable than those from cells grown on the cover slips. This is understandable in terms of the small volume of the sub-cellular aqueous compartment compared to the volume of the chamber; small changes in transport of carbon dioxide and protons across cell membranes can cause larger changes in pH in smaller volumes.

The effects of PMA on steady-state potential are particularly interesting in light of the fact that PMA is known to disrupt the tight junctions responsible for the resistive sealing between these cells. One would expect, therefore, PMA to short out the effects of trans-cellular potentials and to make the composition of the sub-cellular space more like that of the general flow chamber fluid.

EXAMPLE 5

Cyanide ($CN^-$) is a anion that binds to the oxygen combining site of cytochrome oxidase and inhibits electron transport (thereby inhibiting cell respiration). Cells become glycolytic after being exposed to $CN^-$. L Cells (a mouse fibroblast cell line) were grown to confluence on the silicon sensor surface of the flow chamber and exposed to an injection of 100 μM sodium cyanide. Within minutes, the metabolic rate increased 39 % above the rate when the compound was introduced, and then the rate began to gradually decrease. At this point, the cells were rounded up and beginning to die.

EXAMPLE 6

Figure 17:
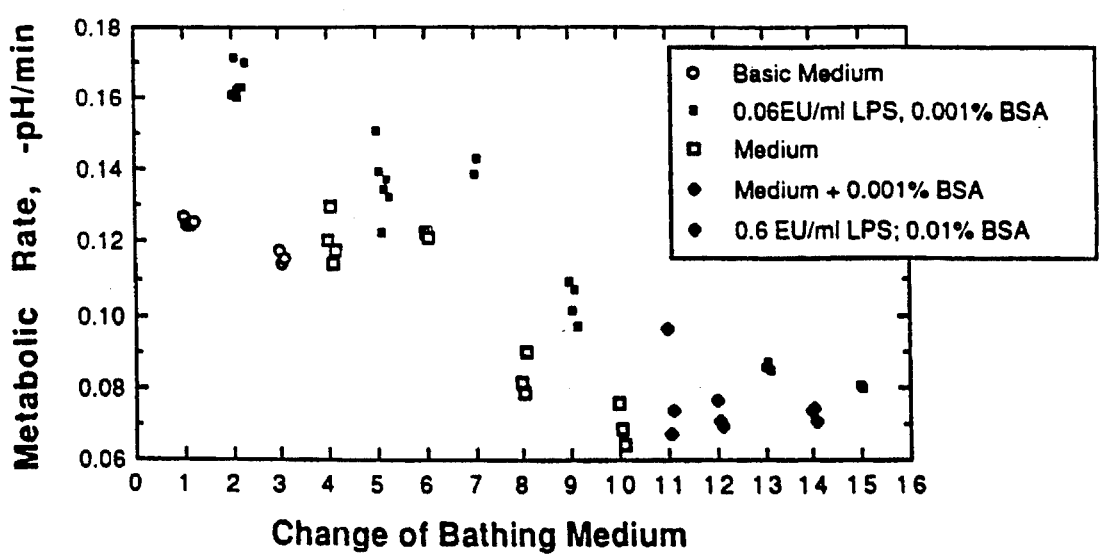

BHK cells (a fibroblast line from baby hamster kidneys) were grown on the silicon sensor surface of the flow chamber and alternately perfused with normal medium and medium containing 0.6 or 0.06 E.U. of bacterial lipopolysaccharide endotoxin. As shown in FIG. 17, the introduction of 0.06 E.U. of endotoxin (with 0.001 % BSA as a protein carrier) resulted in a 31 to 36 % increase in metabolic rate over the rate obtained when the cells were in the presence of medium only (control value). The metabolic rate remained unchanged (with respect to the rate observed when cells were in the presence of medium only) when medium with 0.001 % BSA (bovine serum albumin) or medium with 0.01% BSA plus 0.6 E.U. of endotoxin was introduced. This result may reflect a biphasic response of BHK cells to endotoxin. This is frequently seen for receptor mediated stimulation of cells. A low dose of stimulant gives a response whereas a very high dose can give no response or an opposite response compared to a low dose.

EXAMPLE 7

Amiloride is a diuretic drug that has been used extensively as an inhibitor of the $Na^+$ channel of transporting epithelial cells present in the kidney and the toad bladder. Taub et al. demonstrated that the MDCK cell line possesses an amiloride-sensitive $Na^+$ channel characteristic of the cells present in the distal tubule of the kidney (*J. Cellular Physiology*, 106:191–199 (1981)). When MDCK cells were grown on the cover slip portion of the flow chamber, the introduction of 1.5 mM amiloride resulted in a gradual increase of metabolic rate up to 16 % above the rate observed for medium only. Once exposure to the drug was ceased, the rate returned to the original control value and then gradually continued to decline.

When MDCK cells were grown on the silicon sensor surface of the flow chamber, the introduction of 1.5 mM amiloride resulted in an immediate 20 % decrease in apparent metabolic rate with respect to the rate observed in the presence of medium only.

Interpretation of the data collected from MDCK cells was made difficult by the fact that as cell respiration made the medium more acidic (after medium flow was stopped), the cells responded to the change in pH thereby resulting in a change in the original metabolic rate, to which the cells could also respond. This complicated cell response resulted in a multiphasic curve when medium flow was stopped for a period of time. In the case where the cells were grown on the silicon sensor surface, this phenomenon was particularly dramatic.

EXAMPLE 8

Theophylline (a diuretic, cardiac stimulant, and smooth-muscle relaxant) has been shown to inhibit phosphodtesterase, which results in an increase in the amount of cAMP in the cell. When MDCK cells were grown on the silicon sensor surface, the introduction of 10 mM theophylline resulted in a 47 % decrease in the metabolic rate with respect to the control value. After the theophylline containing medium was removed, the metabolic rate returned to the control value within ten minutes. While the therapeutic level of theophylline (111 μM) introduced to MDCK cells grown on the silicon sensor surface resulted in an approximate 10% decrease in metabolic rate, a 28% increase in rate with respect to the control values was observed when theophylline was removed from the cell environment.

MDCK cells grown on a cover slip demonstrated a similar decrease in the metabolic rate (59%) when the cells were exposed to 10 mM theophylline, although a gradual increase in rate was observed (up to only 48% below the control value). Once the theophylline was removed from the cell environment, the metabolic rate increased 30% over the control value.

EXAMPLE 9

Figure 18:
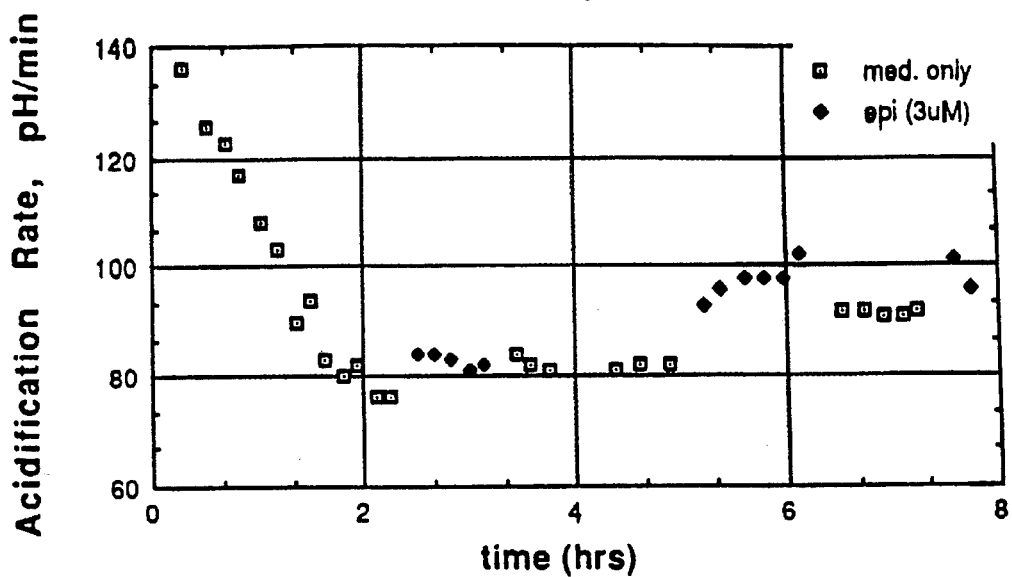

MDCK cells are known to have epinephrine receptors on their basolateral surface (the surface of the cells which attaches to the substrate on which they are growing). Therefore, when MDCK cells are grown on the silicon sensor surface, the epinephrine receptors are oriented on the sensor side of the cellular monolayer. When medium containing 3 μM epinephrine was flowed over the cell monolayer, the epinephrine had to diffuse across the cell layer to reach the receptor. The primary introduction of medium plus epinephrine did not significantly alter the metabolic rate with respect to the control rate. However, as shown in FIG. 18, additional exposure to medium plus epinephrine resulted in a 20 % increase in metabolic rate. The metabolic rate remained 12 % higher than the control rate after the epinephrine containing medium was removed from the cell environment. An additional 7 % increase in metabolic rate was attained when the cells were once again exposed to the epinephrine containing medium (i.e. a 20 % increase in metabolic rate over the control rate).

EXAMPLE 10

Figure 19:
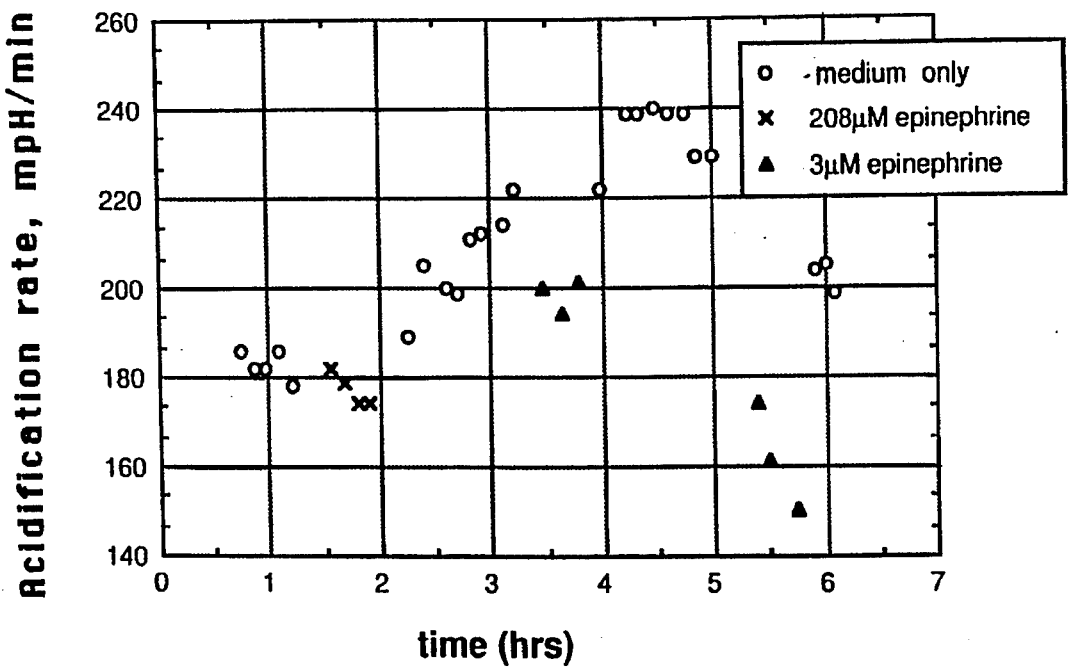

Another method to immobilize cells is to encapsulate them in an agarose gel. MDCK cells in a confluent T-75 flask were trypsinized in order to remove them from their growth container. The cells were centrifuged at 2000 RPM for 5 minutes and the supernatant was discarded. The cells were resuspended in 5 mL of medium and centrifuged for 5 minutes at 3000 RPM. The supernatant was again discarded, and the cells were resuspended in 500 μL of 1.2 % sea plaque agarose from FMC (in medium). The cells were centrifuged for 3 minutes at 3000 RPM to pellet the cells. A 2 μL aliquot was taken directly from the cell pellet and spread over an approximate area of 40 mm² on the silicon sensor surface (in a partially assembled chamber). The chamber was refrigerated for 15 minutes in order to allow the agarose to gel. The assembly of the flow chamber was then completed and the cells were alternately perfused with medium only, medium plus 208 μM epinephrine, or medium plus 3 μM epinephrine. The presence of 208 μM epinephrine resulted in a 3 % decrease in the metabolic rate with respect to the rate observed for medium only. However, as shown in FIG. 19, the removal of the epinephrine from the cell environment resulted in a 14 % increase in metabolic rate over the control rate. Similarly, the introduction of 3 μM epinephrine to the cells resulted in a 4.5 % decrease in metabolic rate with respect to the rate observed immediately after the higher epinephrine concentration was removed. When the 3 μM epinephrine was removed from the cell environment, the metabolic rate increased 17 % over the rate observed prior to its introduction.

EXAMPLE 11

Figure 20:
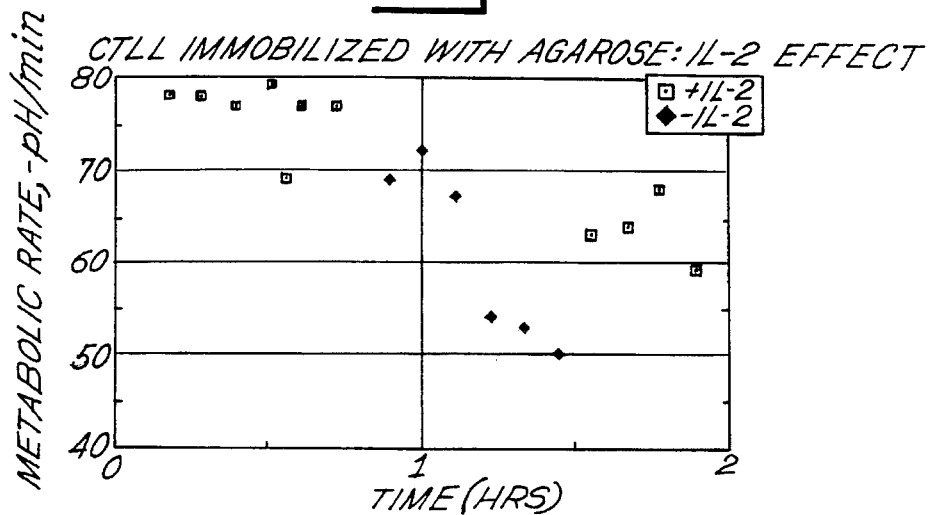

CTLL cells (a cytotoxic T-Cell line from mice) are a nonadherent cell line that requires the presence of Interleukin-2 (IL-2 ; an immune modulator) to remain viable. Two mL of cells were removed from a confluent T-25 flask of CTLL cells and centrifuged to pellet the cells. The supernatant was discarded and the cells were resuspended in 300 µL of a 2 % agarose solution (in medium). The cells were again centrifuged to a pellet, and a 2 µL aliquot was removed from the cell pellet and spread over an approximate 40 mm$^2$ circle on a cover slip that was housed in a humidified chamber. The cover slip chamber was then refrigerated for 20 minutes to allow the agarose to gel. The cover slip was removed from the humidified chamber and placed in a flow chamber. Medium containing 20 units/mL of IL-2 or medium only was alternately flowed across the cells. When the medium containing IL-2 was removed, as shown in FIG. 20, the metabolic rate began to decline with respect to the control rate. The rate continued to decline until medium containing IL-2 was reintroduced to the system, at which time the rate began to increase (although the rate did not return to the control rate value). At this time, the cells were beginning to detach from the agarose gel. As expected, as the cell density decreased, so did the rate of acidification of the chamber.

EXAMPLE 12

L cells were grown to confluence on the silicon sensor surface of the flow chamber and alternately perfused with normal medium and medium containing 0.6 E. U. of bacterial lipopolysaccharide endotoxin. In one experiment the introduction of endotoxin increased the initial metabolic rate 20 % above the rate observed for medium only, and a second exposure of the cells to endotoxin increased the rate 15 % above the rate observed for medium only. In both cases, the rate returned to the initial value when the endotoxin containing medium was removed (within a few minutes).

EXAMPLE 13

Oxytocin is the principal uterus-contracting and lactation-stimulating hormone of the posterior pituitary gland. The introduction of 1 µM oxytocin to MDCK cells grown on a cover slip did not result in any immediate change in the metabolic rate with respect to the control value, although the metabolic rate did gradually decrease (up to 10 %). The removal of the oxytocin from the cell environment did not immediately return the cell metabolic rate to its control value, although within 10 minutes 100 % recovery was attained. This was a control experiment since MDCK cell do not have oxytocin receptors, and oxytocin its a nonapeptide which differs from vasopressin by only two amino acids. MDCK cells do have vasopressin receptors. This was not necessarily the best control experiment because, as shown below, only cells grown on the silicon sensor surface demonstrated a response to vasopressin.

EXAMPLE 14

The introduction of 0.1 µM vasopressin (antidiuretic hormone) to MDCK cells grown in the silicon sensor surface resulted in a 14 % increase in metabolic rate over the control values. The addition of 1 µM vasopressin immediately after the 0.1 µM vasopressin resulted in another increase in the metabolic rate (19 % over the rate attained in the presence of 0.1 µM vasopressin, which is a 42 % increase over the control rate value).

When 1 µM vasopressin was introduced to MDCK cells grown on a cover slip, no increase in metabolic rate was observed.

EXAMPLE 15

The addition of 10 mM MgCl to the control medium resulted in a 40–46 % increase in metabolic rate with respect to the metabolic rate observed when the MDCK cells were exposed to medium only.

EXAMPLE 16

A silicon semiconductor electrode with a nylon mesh adhesively attached to its upper surface, as described above, was prepared. CTLL cells were flowed into the chamber at a flow rate of approximately 10 µL/min. At this flow rate some of the cells settled by gravity into the holes in the nylon mesh. The flow rate was then increased to approximately 100 µL/min and the cells remained in the holes. Cells could be visualized in the microscope. The laser beam was directed to three different regions where cells were present and one region where no cells were present. At each site the change in pH with time was measured with the medium flow on and off. The slope of the pH change in µV/sec with the flow off minus the same change with flow on was as follows:

TABLE II

| | (Flow Off-Flow On) | | |
|---|---|---|---|
| Measurement | µV/Sec | S.D. | Cells |
| 1 | −9.7 | .92 | present |
| 2 | −6.2 | .64 | present |
| 3 | −4.4 | .85 | present |
| 4 | +1.7 | .71 | absent |

EXAMPLE 17

This experiment was designed to demonstrate the possibility of determining partial or complete identification of bacteria on the basis of their ability to change the pH of their immediate environment in the presence of several potential carbon source compounds supplied one at a time in a serial manner to a single "catch" of bacteria. While this method of serial delivery of selective substrates has certain potential advantages, parallel delivery of selective substrates to separate catches of bacteria could also be useful under certain circumstances. Furthermore, if bacteria are used for screening for antibiotic susceptibility or antibiotic activity, parallel delivery to separate catches may well be more appropriate because of potential problems of intereactions of drugs.

The bacteria, E. coli and Proteus mirabilis , were prepared as suspensions of about 5×10$^8$ cells/mL in a growth medium and then diluted into a sterile test medium containing glucose (Bactopeptone, 2 g/L; NACl, 5 g/L; $K_2$ $HPO_4$, 1.7 mM; glucose, 1 g/L; pH 7.3 ). With the controlling electrode piston in the raised position, as disclosed in pending U.S. patent application, Ser. No. 876,925, filed Jun. 20, 1986, now U.S. Pat. No. 5,292,846 one mL of bacterial suspension containing a known number of bacteria was flowed through the device such that the cells were retained adjacent to the silicon sensor surface by a Nucleopore membrane situated parallel to the surface. The cells were pulsed with the same glucose containing test medium, the piston was then lowered to decrease the volume surrounding the cells, and the change in pH due to bacterial metabolism was monitored. The piston was then raised and a second test medium containing urea in place of glucose was flowed through. After lowering the piston the pH change was again monitored. This procedure was repeated with medium containing pyruvate as a carbon source.

Figure 21:
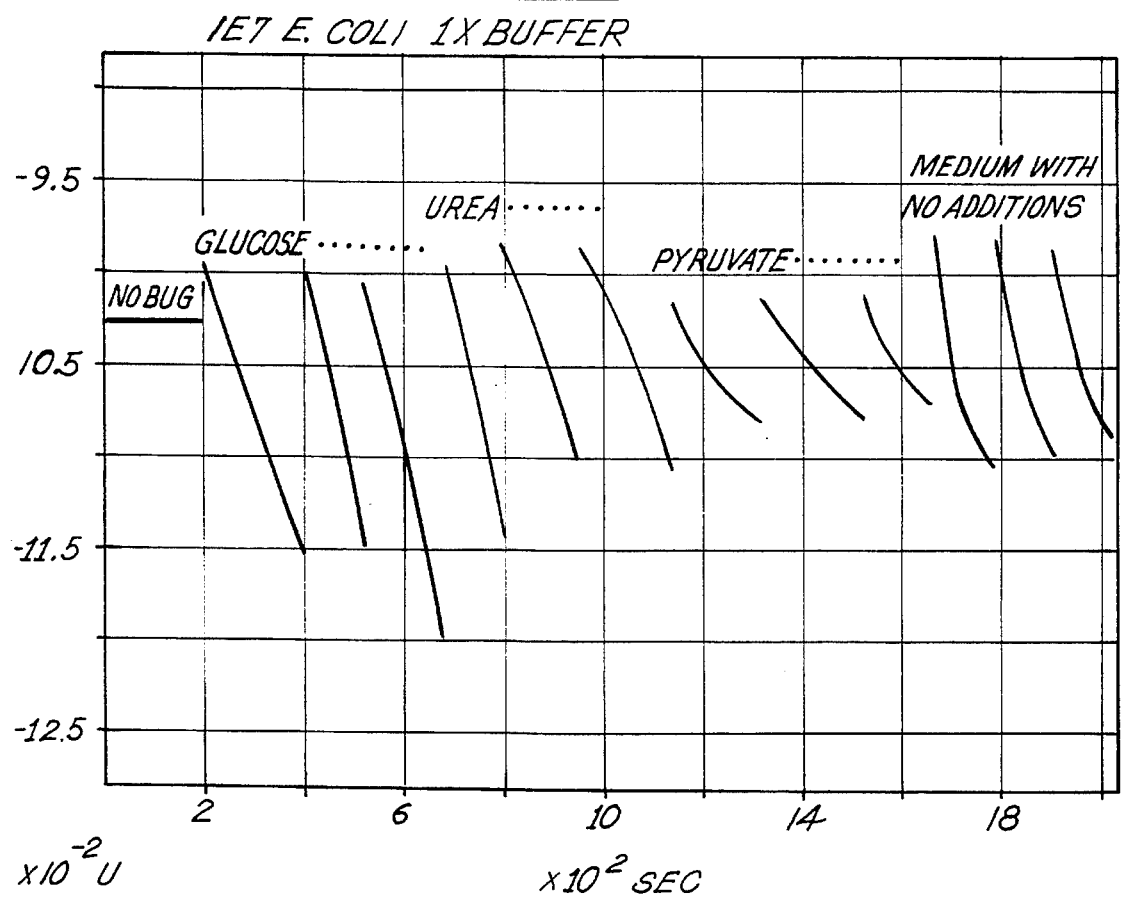
Figure 22:
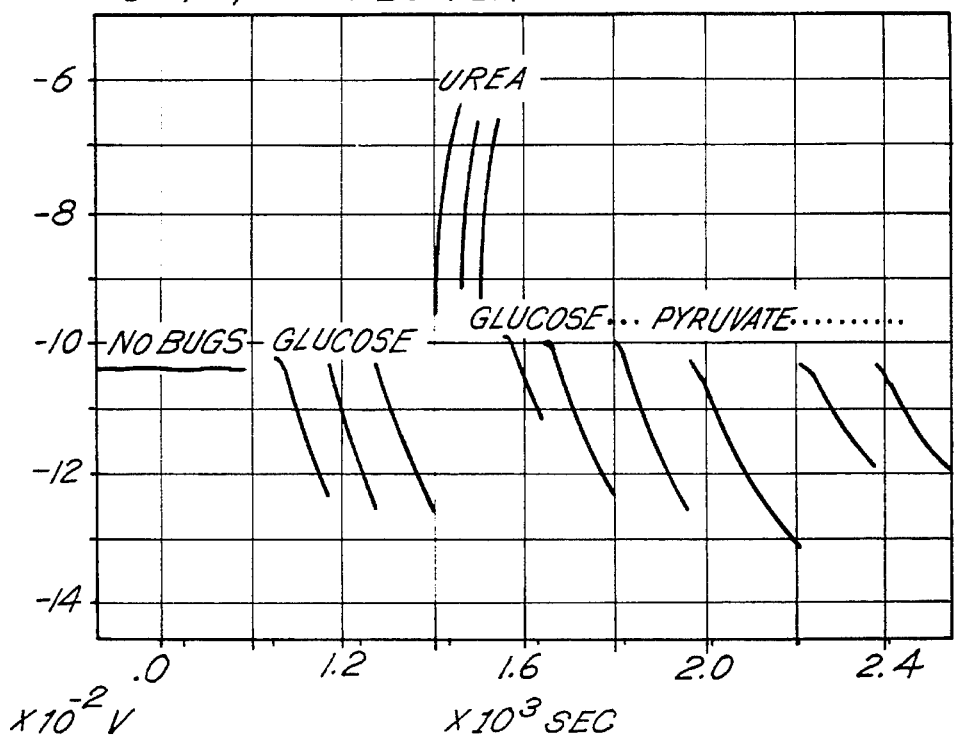
Figure 23:
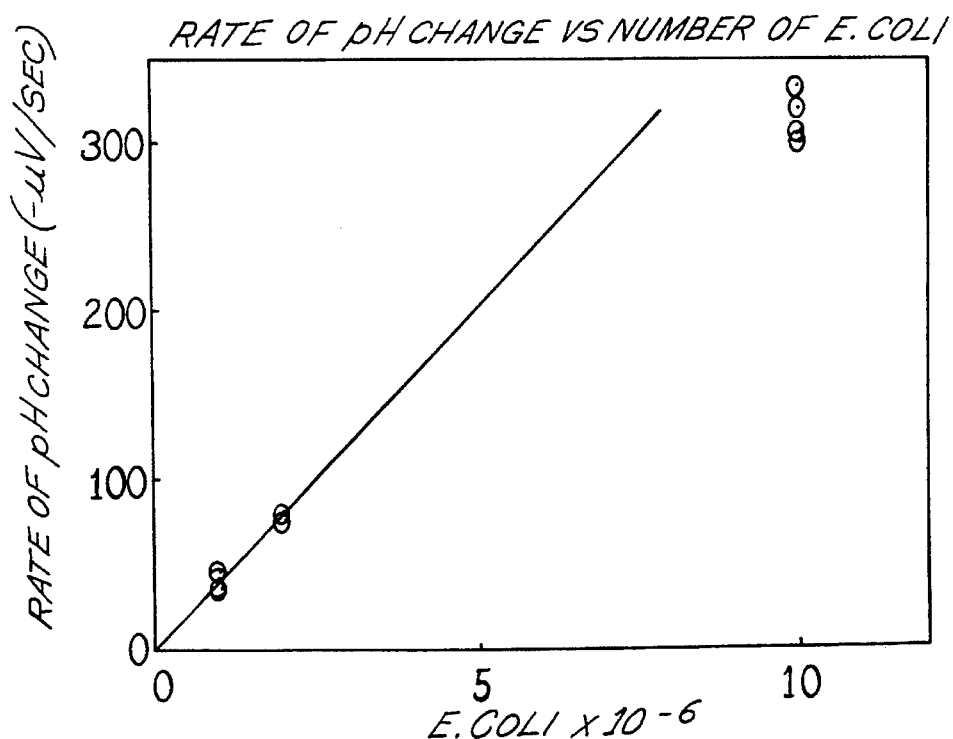

FIG. 21 shows that *E. coli* respond by decreasing the pH in the presence of all three media (each medium was tested three times in succession before testing the next medium). FIG. 22 shows that *P. mirabills* decreased the pH in the presence of glucose and pyruvate, but increases the pH in the presence of urea. FIG. 23 shows that the rate of pH change in glucose medium is dependent on the number of bacteria trapped in the device.

Figure 24:
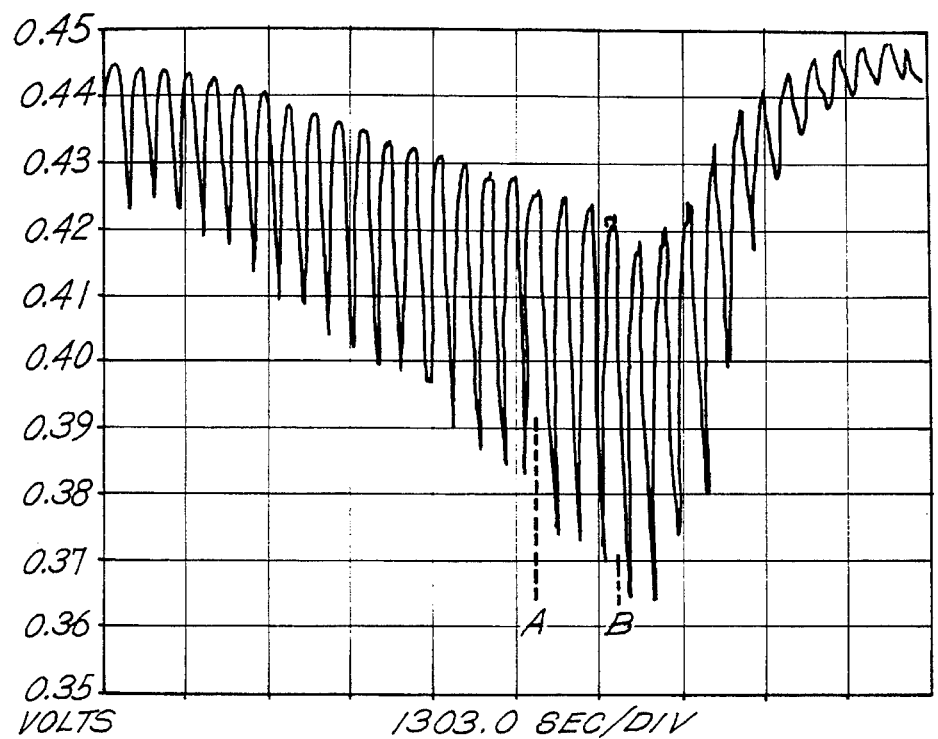
FIG. 24 represents results of exposing gram negative bacteria to an antibiotic which has an effect and one that has no effect on the gram negative bacteria.

FIG. 24 shows *E. coli* in a system that differs from that used for the experiments shown in FIGS. 21 and 22 in that the cells were retained by a membrane, the plane of which was parallel to the flow of the medium rather than perpendicular.

In FIG. 24, the *E. coli* demonstrates an increase in pH change amplihide with time consistent with an increase in the number of bacteria with time. In addition to this apparent demonstration of bacterial replication in the flow cell, FIG. 24 shows that *E. coli* do not respond to an antibiotic that has low activity against gram negative bacteria (penicillin added at point A) but do respond to an antibiotic active against gram negative bacteria (polymyxin added at point B).

EXAMPLE 18

Figure 25:
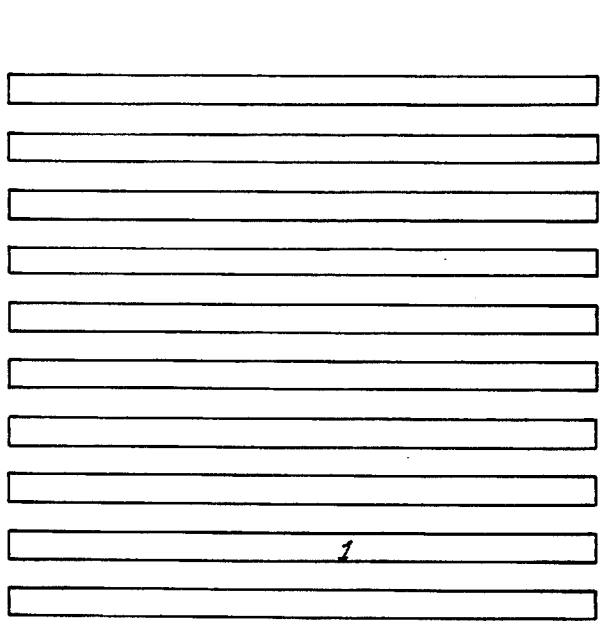
FIG. 25 represents a schematic plan view of wells for retaining cells useful in practicing the preferred inventive methods.

CTLL cells were trapped in the flow chamber in rectangular wells. Referring to FIG. 25, an array 1 of 1000 µm long, 50 µm wide slots, with 50 µm separation between slots, was cut into a 50 µm thick piece of stainless steel foil 2 with an eximer laser. This was mounted in the 100 µm deep flow chamber under pieces of 50 µm thick plastic 3 arranged to press the foil against the silicon semiconductor electrode surface when the cover slip was mounted. This left a channel about 1 mm wide and 50 µm deep above the slots, thereby forming wells.

CTLL cells were settled into the wells at a linear flow velocity of the medium in the channel of no more than about 15 µm/sec. Alternatively, the wells could be loaded by flowing the medium faster than 15 µm/sec. until the cells were suspended above the wells, and then stopping the flow entirely for approximately 10 seconds while the cells sedimented into the wells. This flow/stop procedure was repeated until sufficient cells were trapped.

The cells remained in the wells for flow rates below approximately 100 µm/sec, above which many were flushed out. Alternatively, momentary inversion of the chamber caused the cells to sediment into the flow stream and be flushed away at lower flow rates.

The thin film of liquid between the foil and the silicon electrode, plus possible corrosion of the stainless steel, makes the baseline potential somewhat unstable. This problem could be corrected by micro-machining the wells directly into the silicon semiconductor electrode.

Metabolic rates of −30 to −60 µV/sec were obtained from CTLL cells. This is close to the range observed with adherent cells. Experiments with IL-2 similar to those in Example 11 suggested that after several hours without IL-2 the cells' metabolic rate had decreased to about 20–30 % of its control value; after several hours with IL-2 (20 U/ml) other cells' rate was over 50 % of the control value. This is an indication that the presence of IL-2 can be detected on the time scale of a few hours. Optimization of the apparatus may shorten that time considerably.

EXAMPLE 19

Three cell lines, provided by Dr. Craig Venter at the NIH, have enabled us to detect the functional interaction of agonists and antagonists with specific receptors. The basic cell line, called B82, is a derivative of the L cell line (mouse fibroblast line) and is thought to contain only one natural receptor (the prostaglandin $E_1$ ($PGE_1$) receptor). These cells function only as a control for our experiments.

We have also obtained the cell line with two different transfections. The line designated M1C-2 is the B82 line into which a rat $M_1$ muscarinic receptor has been transfected. The line designated 821 is the B82 line into which a human $\beta_2$-adrenergic receptor has been transfected. Venter and coworkers have determined that the transfections are functional, in the sense that agonists stimulate the appropriate second-messenger systems (phosphoinositol for M1C-2, cyclic AMP for 821). The characterization of these and similar cells can be found in Fraser, C., Chung, F.-Z., and Venter, J. C. (1987) Continuous high density expression of human $\beta_2$-adrenergic receptors in a mouse cell line previously lacking β-receptors J. Biol. Chem. 262:1483–1486 ; Mei, L., Lat, J., Roeske, W., Fraser, C., Venter, J. C., and Yamamura, H. (1989) Pharmacological characterization of the $M_1$ muscarinic receptors expressed in murine fibroblast B82 cells. J. Pharmacol. Exp. Therapeutics 248:661–670.

Each of the three cell lines is grown in F-12 DME medium supplemented with 10 % fetal bovine serum. Geneticin (50 µg/ml) is always included in the 821 cells' medium to prevent a reversion of the transfection. The cells of interest are plated on indium-tin oxide coated cover slips and allowed to grow to 60–90 % confluence. Sixteen to twenty-four hours prior to the experiment, the growth medium is removed and replaced with medium containing no fetal bovine serum. In the case of the M1C-2 cells, 1 µM dexamethasone is added with the serum-free medium and in subsequent steps to induce the transcription of the $M_1$ gene which is under the constitutive control of the dexamethasone-inducible MMTV promoter.

After the cells have been serum starved, the cover slips are loaded into the flow chamber with the cells facing the silicon sensor. Low-buffered medium (F-12 DME without sodium bicarbonate or HEPES buffer added) is flowed through the cell chamber at ~100 µl/min. The cell chamber is kept at 37° with a flow cycle of 300 sec on and 200 sec off. The cells are allowed to equilibrate in control medium for two to three hours before the introduction of the agonist. Time zero on the following graphs indicate the time at which agonist and/or antagonist was introduced to the cell chamber.

Figure 26:
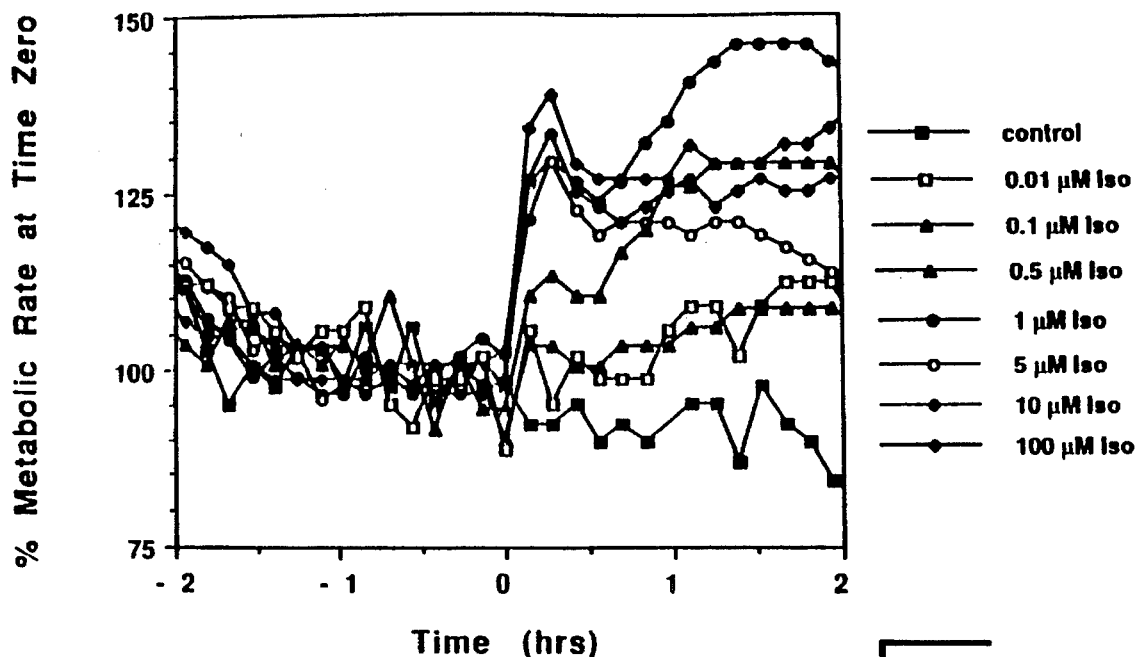

FIG. 26 is an example of an isoproterenol dose-response curve using 821 cells. The cells exposed to the control medium remained relatively constant, whereas isoproterenol caused a rapid increase in the metabolic rate, peaking within the first 30 minutes. A dose-response relationship was observed.

Figure 27:
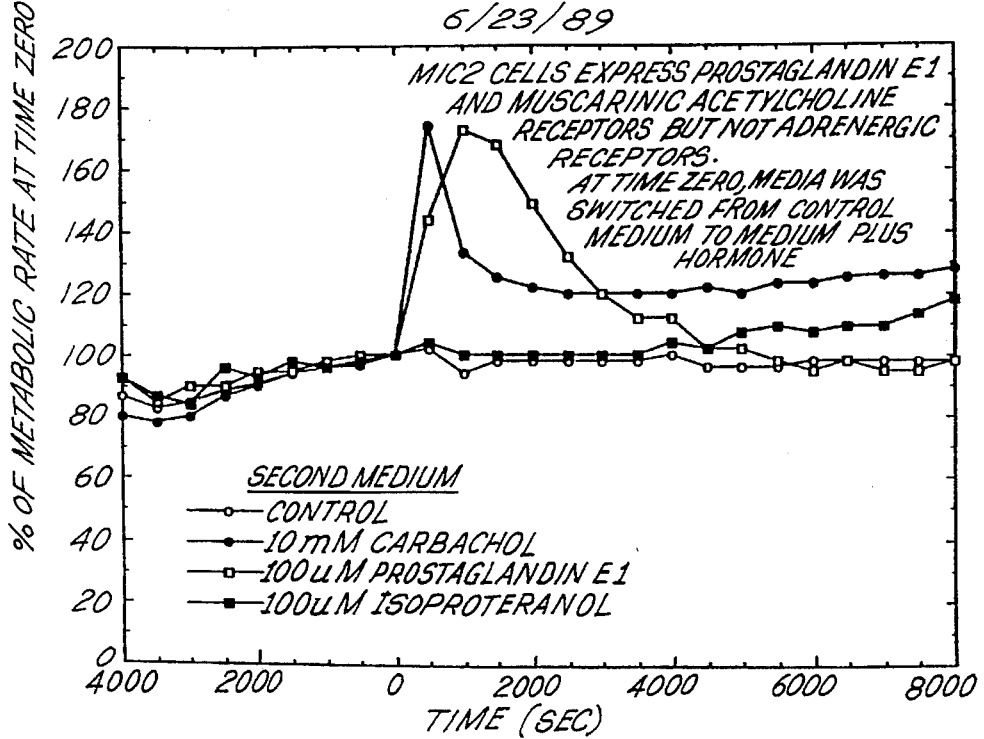

FIG. 27 shows the effect of carbachol (an $M_1$ agonist), $PGE_1$ , and isoproterenol on M1C-2 cells, which contain both the $M_1$ muscarinic and $PGE_1$ receptors. Carbachol caused an 80 % increase in metabolic rate, which peaked in approximately 50 seconds and dropped back to a steady state level of approximately a 40 % increase in metabolic rate in 200 seconds. Stimulation of M1C-2 cells with $PGE_1$ resulted in an 80 % increase in metabolic rate that peaked in approximately 1000 seconds and returned to base line metabolic rates in 4000 seconds. The difference in the peak timing can be attributed to the fact that the binding of $PGE_1$ to the $PGE_1$ receptor affects a different second-messenger pathway (cyclic AMP) than does the binding of carbachol to the muscarinic receptor. FIG. 27 also demonstrates the lack of $\beta_2$-adrenergic receptors in M1C-2 cells, since the introduction of isoproterenol had no effect.

FIG. 28 demonstrates agonist-antagonist interactions with the muscarinic receptor in M1C-2 cells. The introduction of 10 mM carbachol (a muscarinic agonist) to M1C-2 cells resulted in a 75 % increase in metabolic rate with respect to baseline metabolic rates. Atropine, a potent muscarinic antagonist, blocked the response of these cells to carbachol. Atropine alone had no significant effect on the cells.

Figure 30:
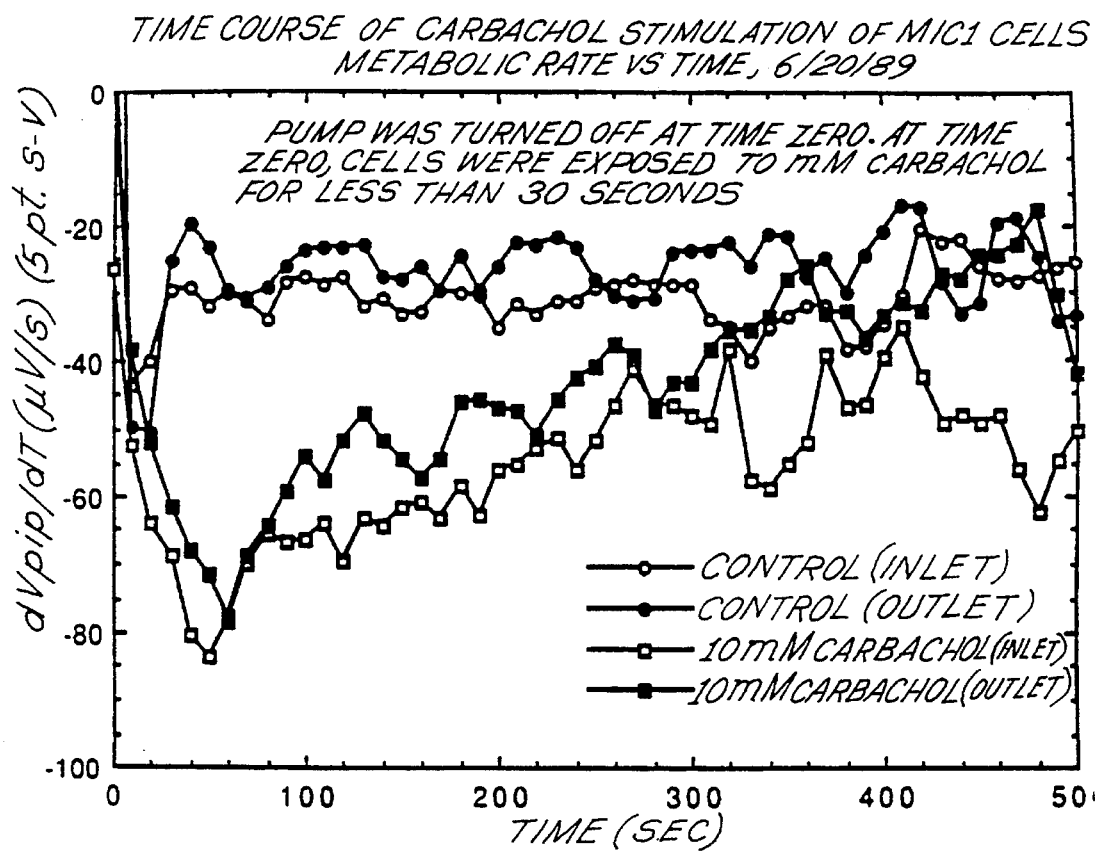

FIGS. 29 and 30 show results obtained with a protocol modified slightly to increase the temporal resolution of the rapid response of the M1C-2 cells to carbachol. Two chambers (one experimental and one control) were assembled with cells and equilibrated as described above, During an off period, the flow rate was changed from 100 μl/min to 200 μl/min. When the flow resumed, an injection valve was switched to introduce carbachol containing medium into the cell chamber. The flow was stopped after 45 seconds and the acidification of the medium was followed (FIG. 29). The time derivative of the sensor potential (equivalent to pH) was calculated using a 5 point quadratic Savitsky-Golay (1964) algorithm and is shown in FIG. 30. (See Savitsky, A., and Golay, M. (1964) Smoothing and differentiation of data by simplified least squares procedures. Analytical Chem 36:1627–1639 .)

Thus, the rate of acidification can be followed with an improved resolution of ~2 seconds over the period in which the flow is off. The duration of this experiment is set by the length of time it takes the cells to perturb the pH and metabolite concentrations of the stagnant medium significantly. At this point, flow must be restored and data collection halted.

The response peak occurred 50–60 seconds after the cessation of medium flow. It should be noted that because a 5 point Savitsky-Golay algorithm was used in the calculations, the first few points are not valid; they include data points during the time of medium flow.

The control cells in this example is the B-82 cell line, a murine fibroblast cell line. The B-82 cells contain a prostaglandin $E_1$ receptor. They do not contain either muscartnic or adrenergic receptors. B-82 cells have been transfected with the human beta$_2$ -adrenergic receptors (821 cells) and with rat $M_1$ muscarinic cholinergic receptors (M1C-2 cells). The cell lines were provided by Dr. J. C. Venter. All the above mentioned cell lines are grown in F-12 DME with 10 % Fetal Bovine Serum (FBS). The transfected 821 cell growth medium contained 50 μg/ml geneticin to prevent reversion of the transfection. Geneticin its included in the low buffered experimental medium also. Each of the cell lines are plated on indium-tin oxide covered cover slips and allowed to grow to 85–100 % confluence. Approximately twenty-four hours prior to the experiment, the growth medium is removed and replaced with serum depleted medium. In the case of the M1C-2 cells, 1 μM dexamethasone is added to the serum depleted medium.

The cover slips are then loaded into the flow chamber with the cells facing the silicon sensor. Low buffered medium is flowed through the chamber (kept at 37°). 821 cells are exposed to medium with 50 μg/ml geneticin. M1C-2 cells are exposed to medium with 1 μM dexamethasone. B82 cells are exposed to medium with 0.5 % ethanol (because ethanol is needed to dissolve PGE$_1$). After the cells are allowed to equilibrate for approximately 2 hours, the receptor agonist of interest is introduced (100 μM PGE$_1$ is introduced to B82 cells, 10 μM isoproterenol to 821 cells, and 3.12 μM carbachol to M1C-2 cells). Time 0 on these figures indicates where the valves are switched to introduce the agonists. It should be noted that there is a slight delay before the agonist actually enters the flow chamber.

EXAMPLE 20

Figure 31:
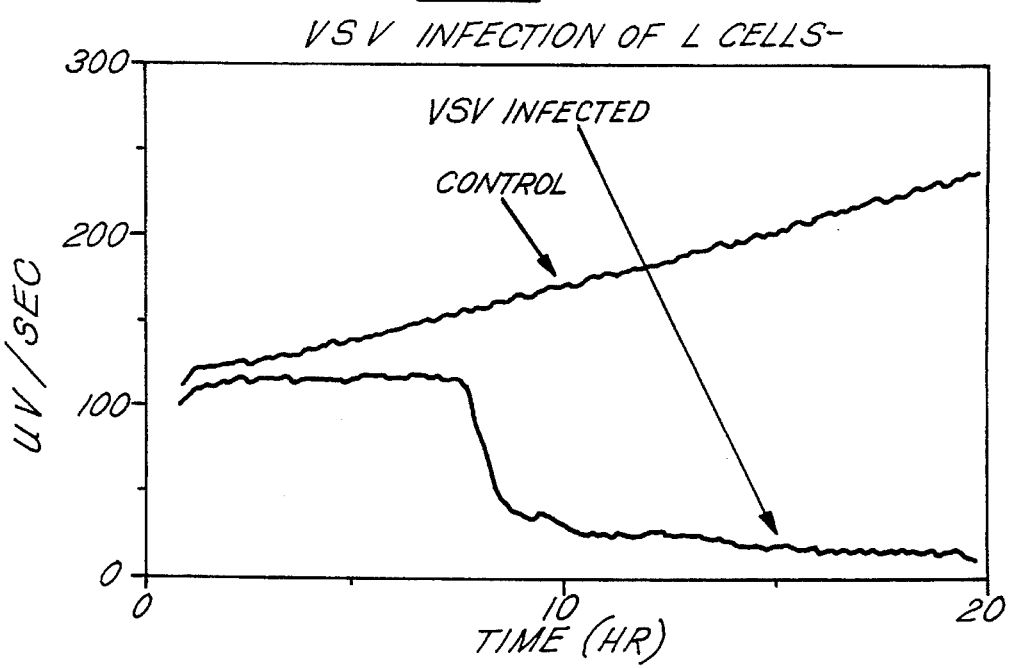
Figure 32:
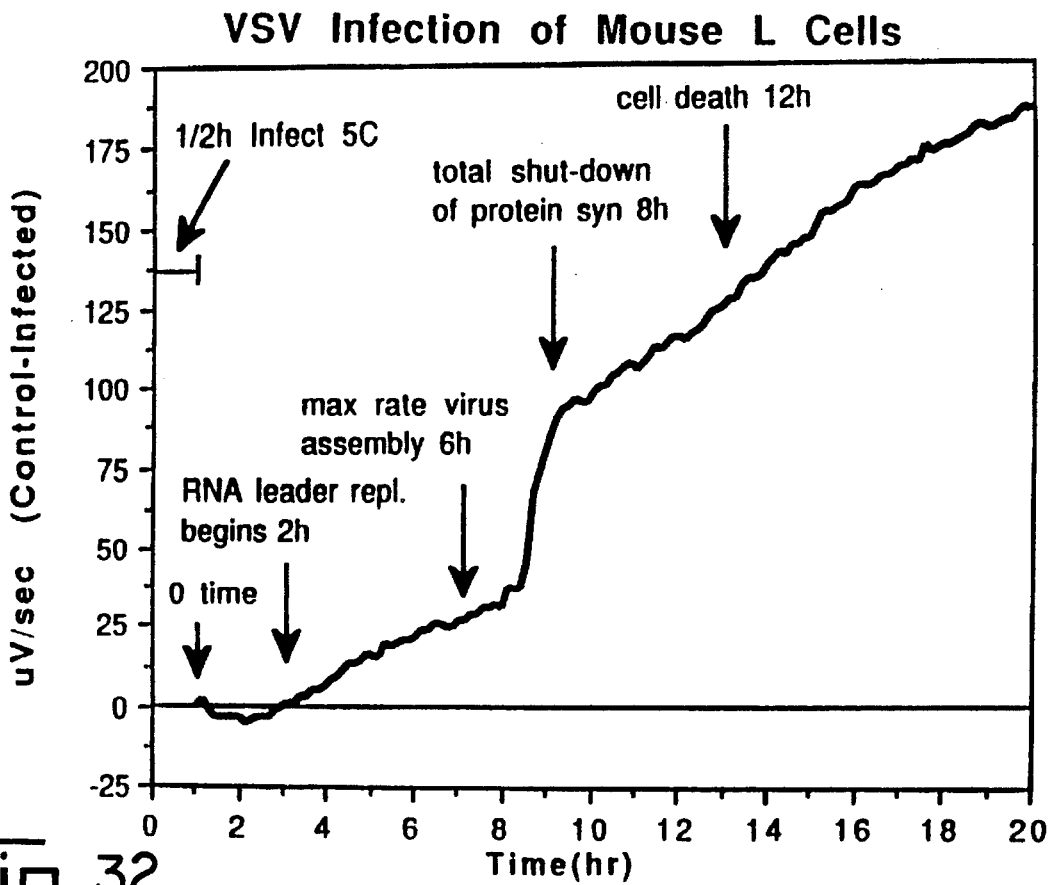
Figure 33:
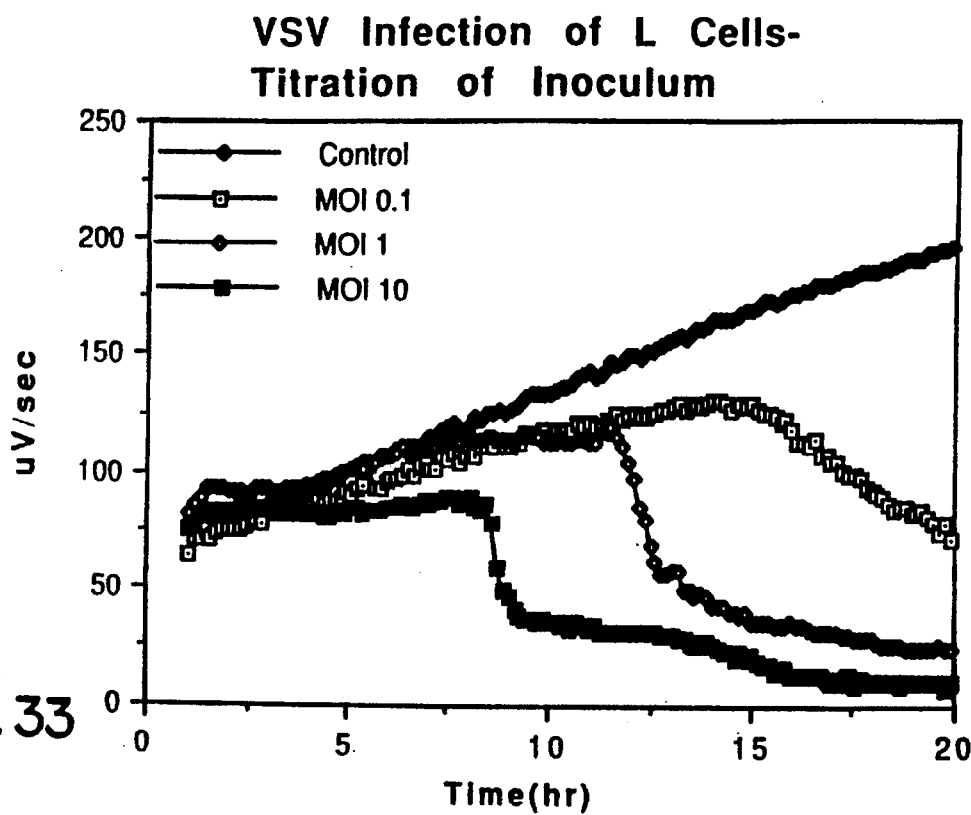
Figure 34:
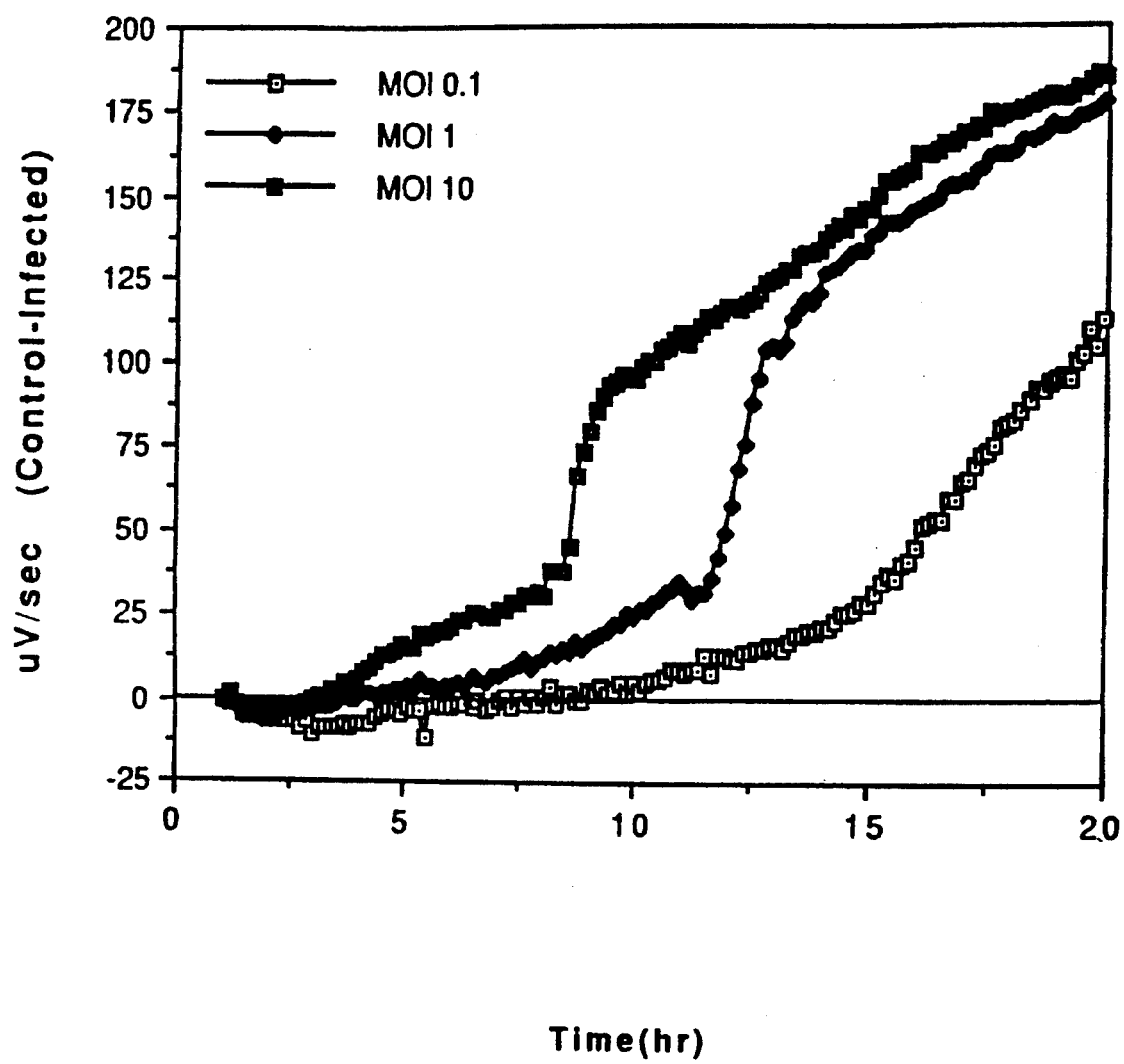
Figure 35:
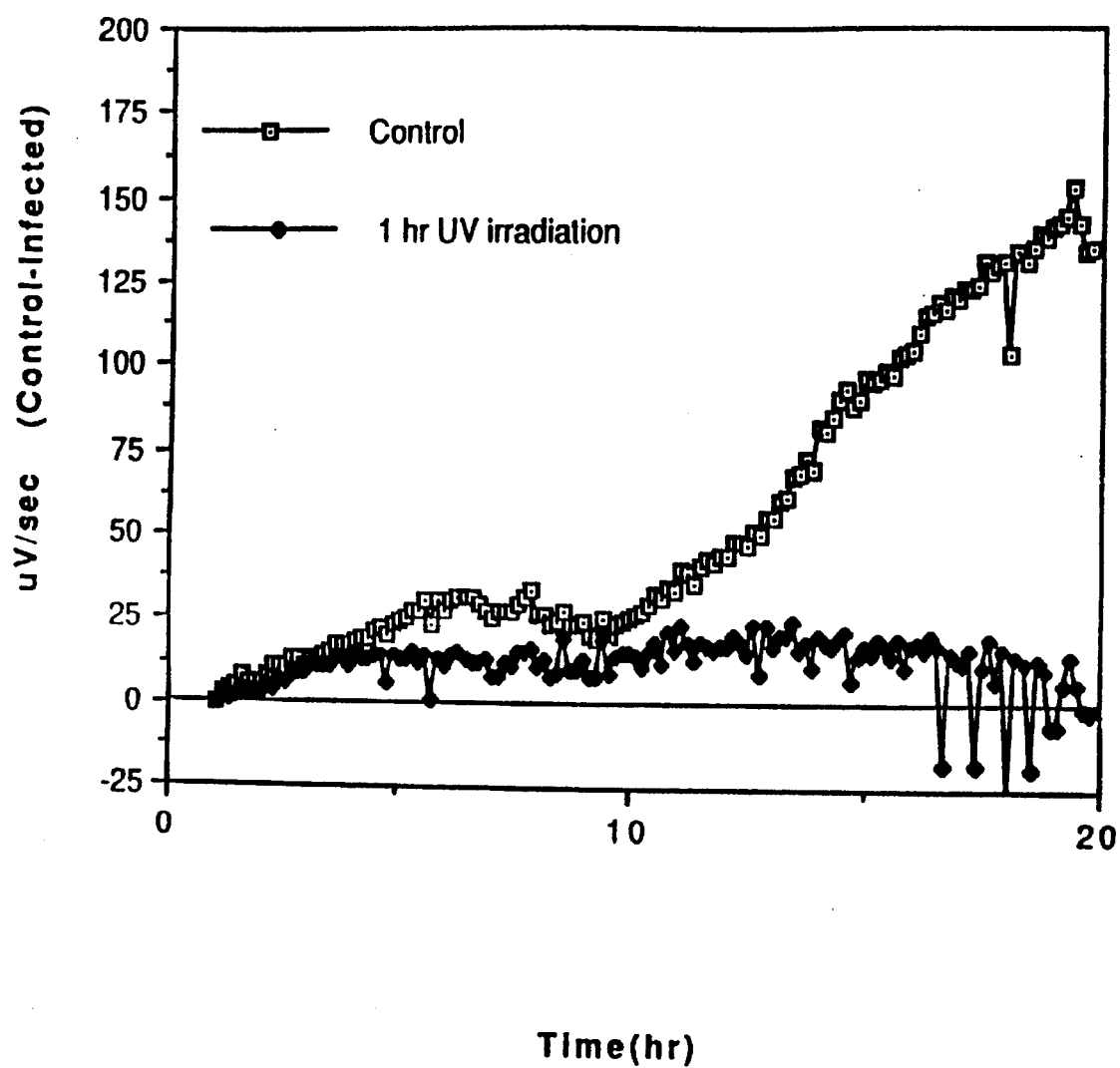
Figure 36:
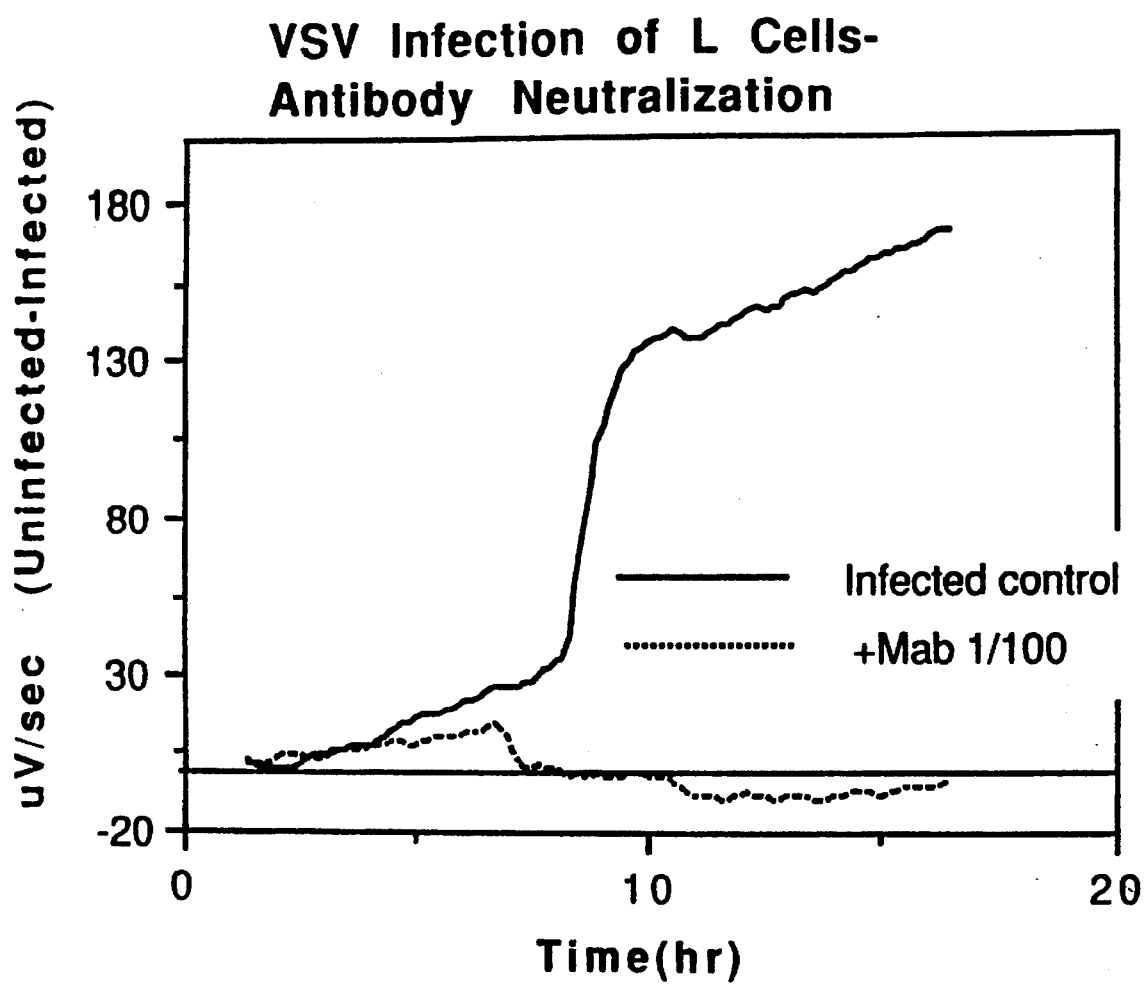
Figure 37:
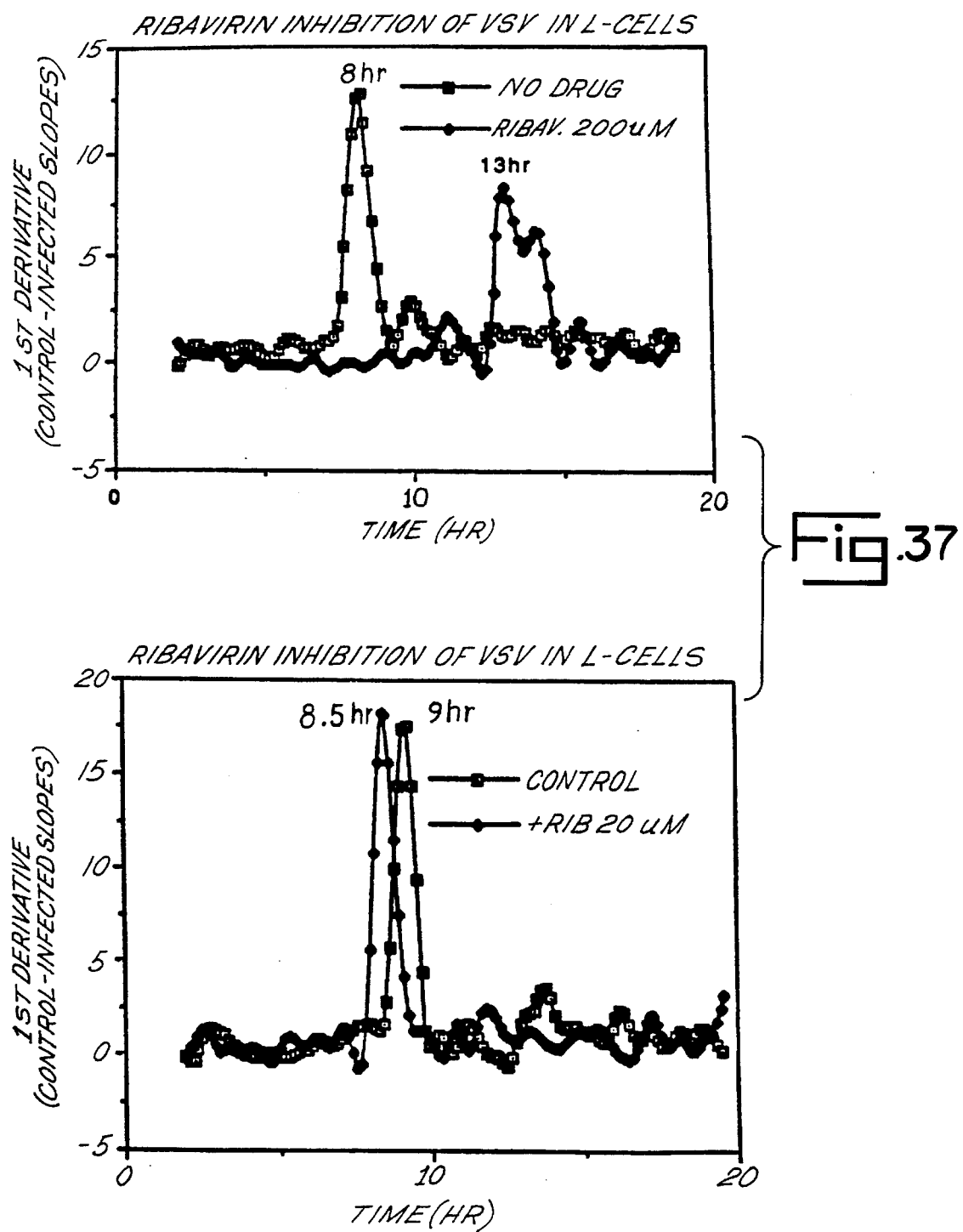
Figure 38:
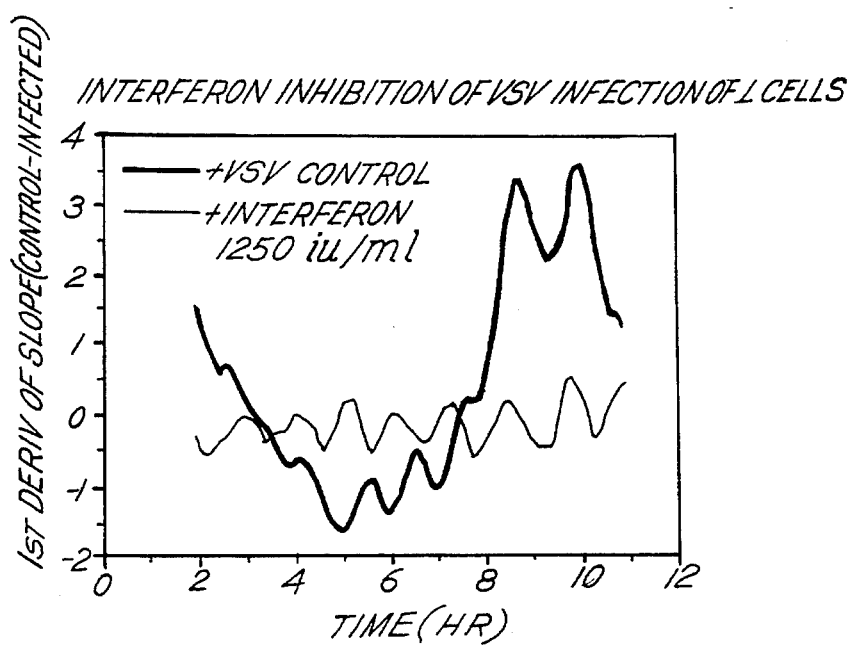
Figure 39:
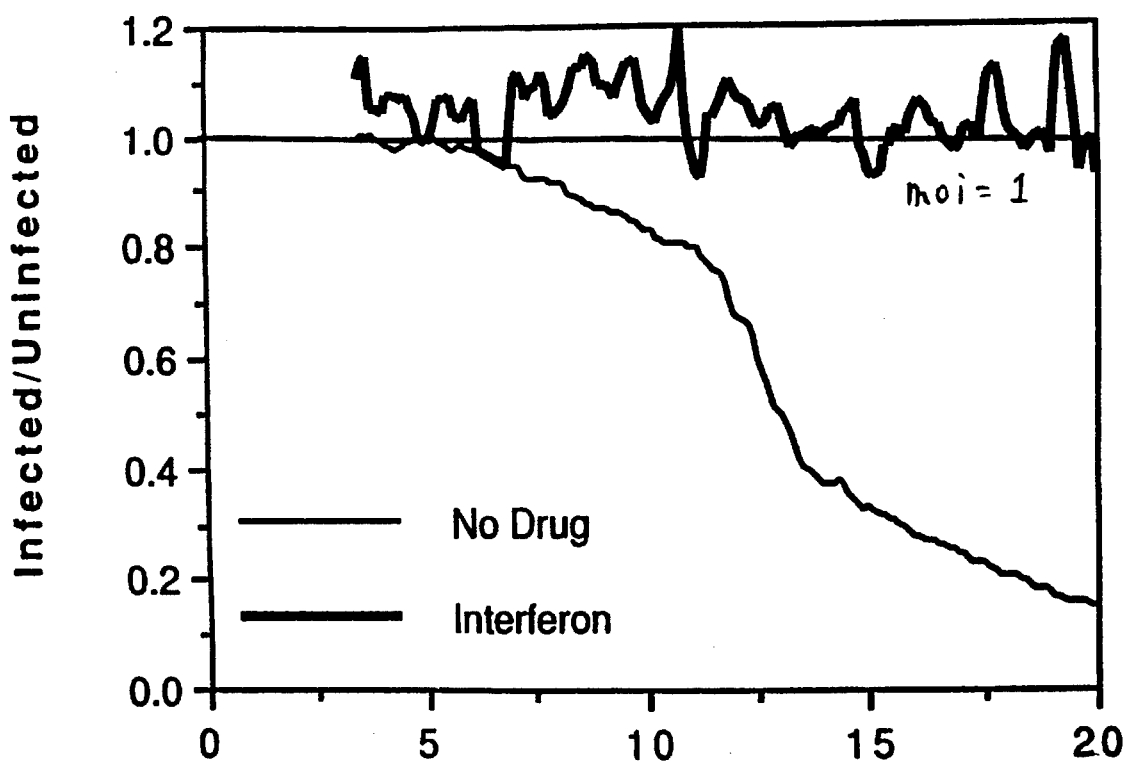

The infection of cells in tissue culture by vesicular stomatitis virus (VSV) results in the alteration of cellular metabolism as a consequence of shut-down of protein and RNA synthesis. The result of viral infection and replication is cytolysts of host cells, which is preceded by cytopathic effects, i.e., cell swelling and rounding. These morphological consequences of infection can be used to detect virus replication in cell culture. In theory, modification of host cell metabolism could also be used to detect and monitor viral replication. In the present example, a silicon-based biosensor, which measures production of acidic metabolites, has been used to monitor metabolism of mouse L cells during VSV infection. Infected and uninfected cells are held in a thin (100 μm) flow chamber which enables sensitive and quantitative measurement by the biosensor of medium acidification during stopped flow conditions. Between metabolic measurements, fresh medium is perfused through the flow chamber to maintain the cells under optimal growth conditions. Using the biosensor system, a depression in L cell metabolic rate was detected between 2–4 hours post VSV infection and a precipitous drop in rate occurred later in the cycle, 8–14 hours post infection (See FIGS. 31 and 32). The extent and time at which host cell metabolism decreased were found to be a function of multiplicity of infection (See FIGS. 33 and 34). The specificity of the VSV effect on host cell metabolism was confirmed by sensitivity to UV irradiation of viral inoculum (See FIG. 35), by neutralization with monoclonal anti-VSV antibody (See FIG. 36), and by inhibition when ribavirin was included in the medium (See FIG. 37). We have also demonstrated the protection by mouse Interferon of the host L cells from VSV infection, using the biosensor (See FIGS. 38 and 39).

Figure 40:
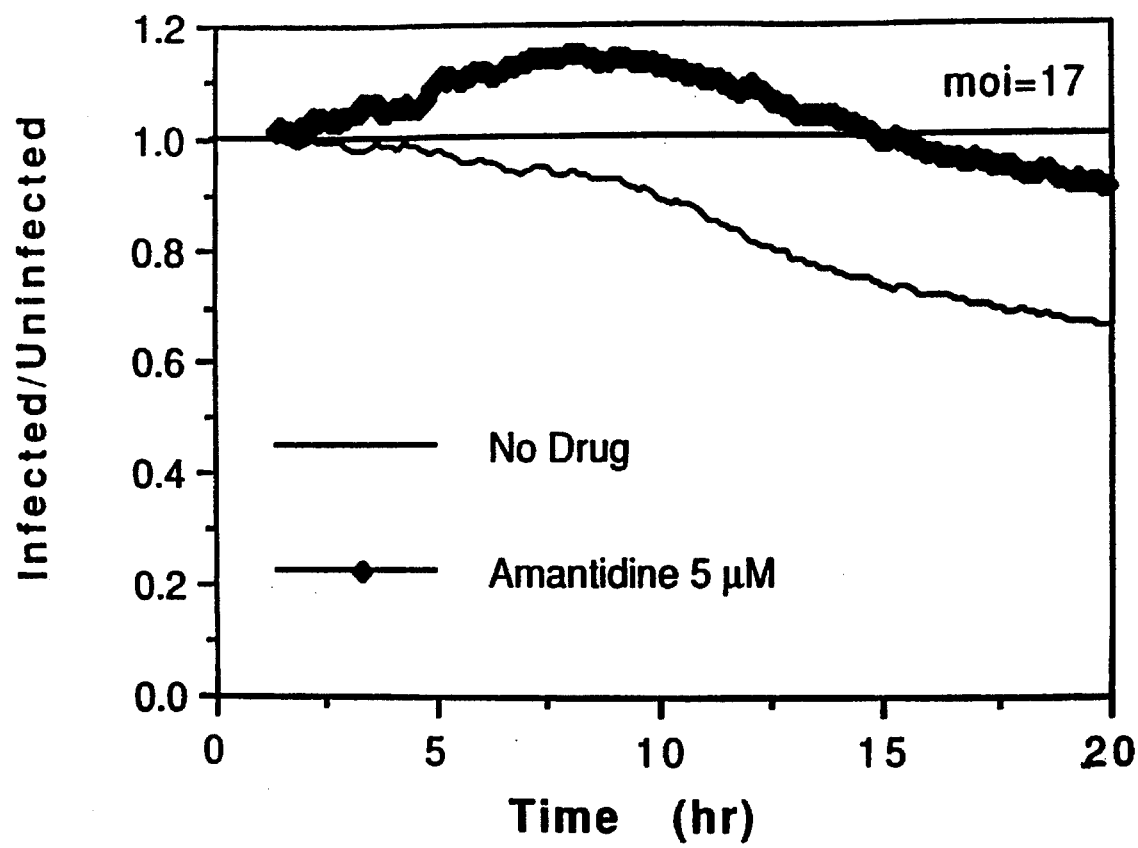
Figure 41:
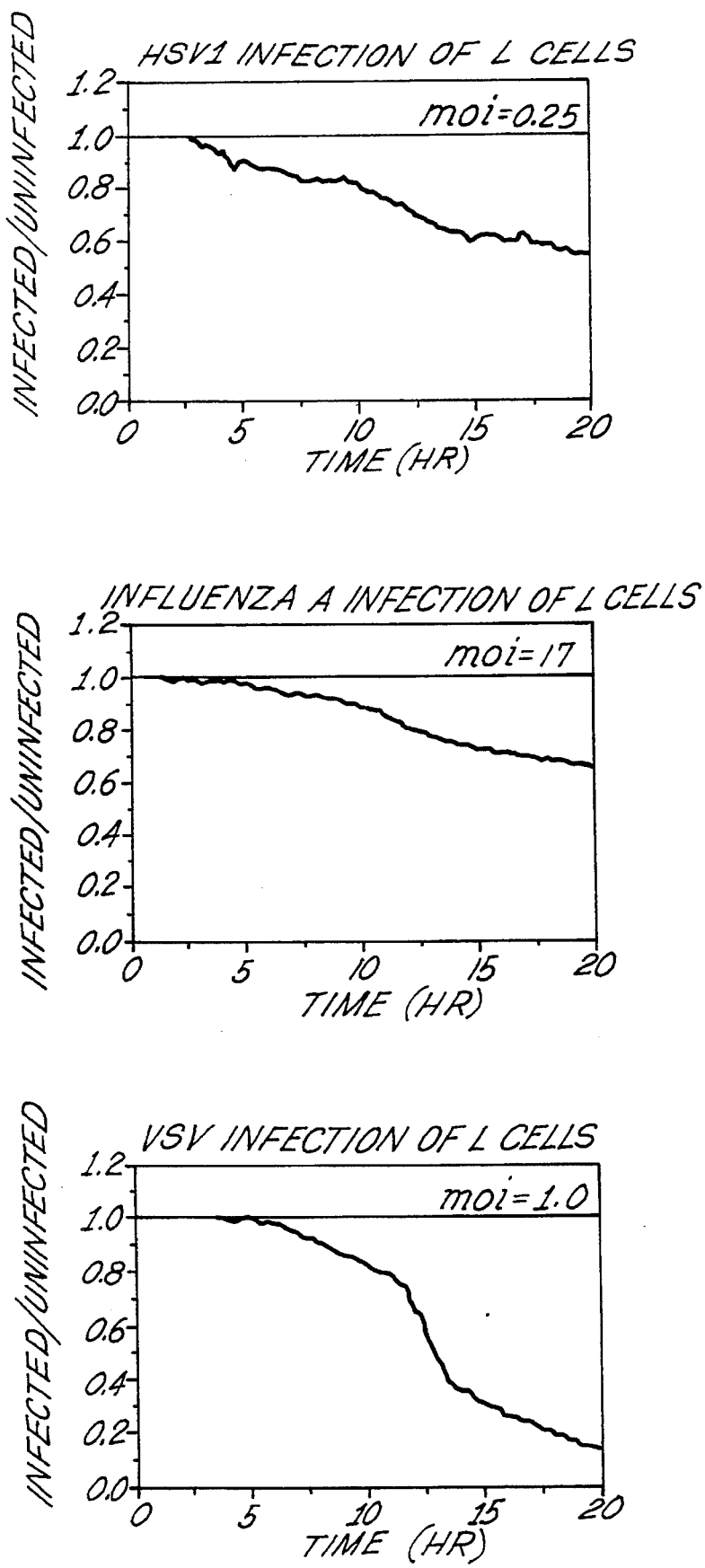

FIGS. 40 and 41 show additional data generated by the infection of L cells by VSV, Influenza A (WSN strain) and HSV-1 . Influenza A is a minus-strand RNA virus that causes influenza in man. HSV-1 is a DNA virus that cause herpes infection in man. Acyclovir may be used to inhibit HSV-1 and amantadine may be used to inhibit influenza A.

EXAMPLE 21

For many types of mammalian cells, a confluent monolayer (equivalent to about $10^7$ cells/mL) commonly produces acidification rates within a factor of two of 100 μV/s. At 59 mV per pH and medium buffer capacity of 1 mM, this corresponds to a calculated net rate of H+ production of $~1 \cdot 10^8$ /s for a typical cell. The metabolic sources of these protons depend on the nutrients in the culture medium and the metabolic pathways that are active in the cells. Some insight into this can be gained using auxiliary biochemical measurements and specific metabolic poisons.

Oxygen consumption was measured in a separate perfusion apparatus equipped with a Clark oxygen electrode. The removal of oxygen from the media by a monolayer of the murine fibroblastic L cell line was measured in the output stream under conditions of constant flow. Lactate production was also measured, using a spectrophotometric enzymatic assay based on the reduction of NAD+. When culture medium was used as the bathing medium, the rates of oxygen consumption (approximately corresponding to $CO_2$ production) and lactate production per cell were found to be roughly equal to $3.1-(\pm 0.3) \cdot 10^7$ /s. Similar results were obtained when the cells were tested in a balanced salt solution with 5 mM glucose as the only carbon source.

The metabolic poison carbonylcyanide chlorophenylhydrazone (CCCP) is a respiratory uncoupler that has been shown to simulate mitochondrial oxygen uptake. FIG. 42 shows the effect of 20 μmM CCCP on the non-adherent murine macrophage-like line P388D1 trapped in etched wells. The stimulation is prompt, faster than the resolution of the apparatus. It is reversible, with a recovery time of about 20 min. after the removal of the uncoupler. Dose-response experiments show a maximum stimulation of the acidification rate near 2–5 μM CCCP, Presumably the mechanism is a combination of increased $CO_2$ production and the stimulation of glycolysis to maintain homeostasis.

EXAMPLE 22

Normal human keratinocytes require epidermal growth factor (EGF) for proliferation without differentiation. Keratinocytes (from Clonetics, Inc.) were cultured in the absence of EGF for a period of 24 hours prior to the experiment. For the experiment, the keratinocytes were assembled into four flow chambers and the alternating stop-flow sequence was initiated with medium containing no EGF. At the time indicated by the arrow in FIG. 43, the syringes containing medium were changed on all four flow chambers. The second medium contained 5 ng/ml mouse EGF, or 1.25 μg/ml of a neutralizing rabbit anti-mouse-EGF polyclonal IgC, or both. A control with no EGF or IgC was also run. The addition of EGF led to a metabolic burst by the keratinocytes that was neutralized by inclusion of the anti-EGF antibody. Addition of the anti-EGF antibody alone had no effect.

These experiments, the results of which are shown in FIG. 43, demonstrate that the microphysiometer is capable of detecting some ligand-receptor interactions functionally in living cells.

Figure 44:
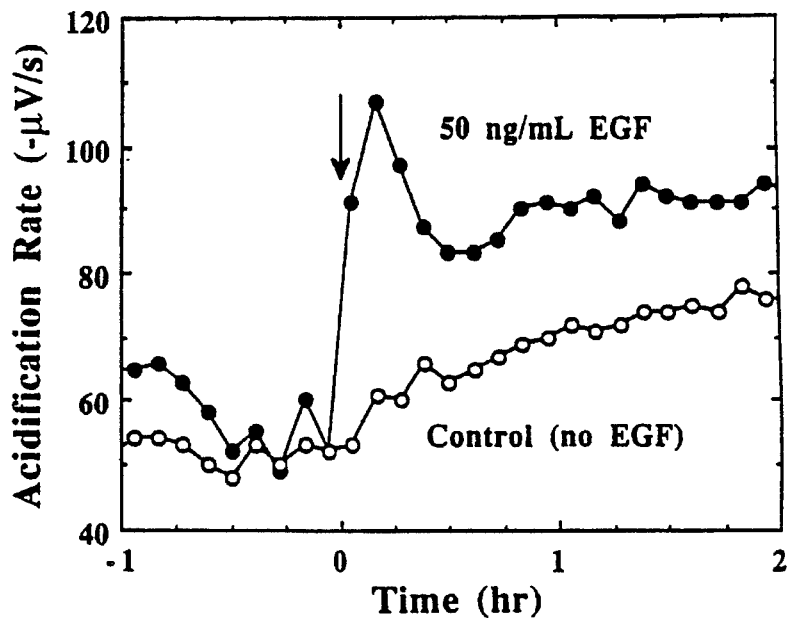

In a separate experiment, the growth medium for the normal human epidermal keratinocytes contained 10 ng/mL murine EGF, a substance found to be mitogenic for keratinocytes. FIG. 44 shows that, after EGF starvation for 24 hr, a rise in metabolic rate is evident within 5 min. after the introduction of 50 ng/mL EGF to keratinocytes in the silicon microphysiometer. At the peak of the response, in ~15 min, the metabolic rate has nearly doubled; in another 15 minutes it has decayed to a steadily rising baseline. A parallel control experiment with a sham change of EGF-free medium, also depicted in FIG. 44, displays none of this biphasic behavior. It does show the same rising baseline, which probably indicates some combination of cell proliferation and adaptation to the environmental conditions in the flow chamber.

Stimulation of acidification rate was observable down to 0.1 ng/mL EGF. In a control experiment, the stimulation was abolished by a monoclonal antibody to EGF that is known to block receptor binding. These experiments demonstrate the ability of the biosensor to detect a cellular response to ligand-receptor binding on a time scale of minutes.

The effects of EGF on keratinocytes closely parallels that previously reported for mouse and human fibroblasts, where stimulation with EGF has been shown to lead to a rapid increase in glycolytic rate. The enhancement in rate has been attributed to increased 6-phosphofructo-1-kinase activity as a result of increased concentrations of fructose-2,6-biphosphate, a potent stimulator of the enzyme. Fructose-2,6-biphosphate has also been shown to play a role in the stimulation of glycolysis in fibroblasts by serum, insulin, and phorbol esters. Modulation of glycolytic rates in response to hormonal activation has been reported in other cell types, including muscle and liver cells, thus lending support to the measurement of metabolic activity as a means of detecting hormonal stimulation.

EXAMPLE 23

The cytotoxic effects of chemotherapeutic drugs on tumor cell lines are commonly determined by assays that detect proliferation. Using a previously characterized cellular system, we have performed cytotoxicity assays in the silicon microphysiometer. MES-SA is a human uterine sarcoma line that is sensitive to doxorubicin and vincristine. The Dx5 line, derived by selection with doxorubicin from MES-SA, is resistant to doxorubicin and vincristine by virtue of enhanced activity of the P-glycoprotein transporter, which confers multidrug resistance.

Figure 45:
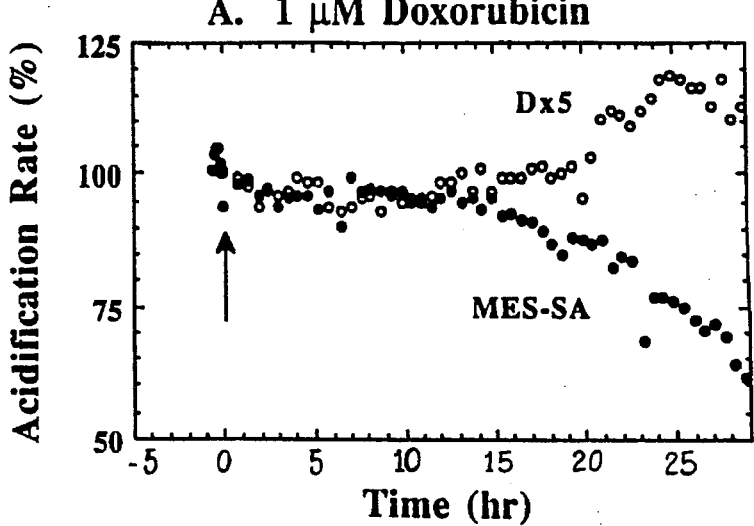
Figure 46:
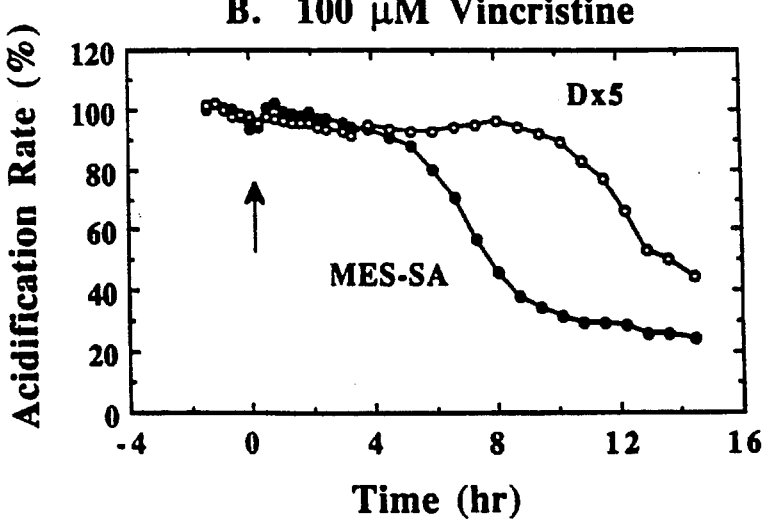

Experiments using the silicon microphysiometer reproduce these results. At therapeutic doses of doxorubicin (1 μM), the differential cytotoxicity in the two lines is maintained. As depicted in FIG. 45, decreased acidification rates are evident at 15 hours MES-SA but not by 50 hours for Dx5. At high (100 μM) doses of the drugs similar but more rapid results occur: cytotoxicity of doxorubicin is manifest by 0.5 hour for MES-SA and 2.5 hours for Dx5. The results for 100 μM vincristine, shown in FIG. 46, are 5 and 10 hours, respectively.

This system requires relatively few cells and no extended cell growth. These factors, plus the ability of making repeated measurements on the same set of cells, suggest additional applications in cytotoxicity testing.

The present invention has been described in terms of certain preferred embodiments. Other embodiments not specifically described herein may nevertheless fall within the spirit or scope of the present invention or the following claims.

We hereby claim as our invention:

1. A method for detecting a pH change effect of a cell affecting agent on living cells comprising:

(a) providing living cells retained in a micro flow chamber having a height of about 50 μm to about 200 μm and having a means for continuous or intermittent flow of a solution or a suspension containing the cell affecting agent in contact with the cells such that the amount of the cell affecting agent in contact with the cells can be controlled;

(b) flowing a solution or suspension containing the cell affecting agent such that it comes into contact with the living cells thereby producing a change in pH of the solution of suspension about said living cells; and (c) repetitively stopping the flow and repetitively measuring the change in pH of the solution or suspension about said living cells when the flow is stopped, by a means for detecting Ph to detect any change in Ph caused by the cell affecting agent on said living cells.

2. A method for screening for the presence or activity of a drug comprising:

(a) providing a micro flow chamber having a height of between about 50 μm and 200 μm with a portion of the micro flow chamber being a silicon semiconductor electrode, said micro flow chamber being adapted for continuous or intermittent flow of a solution or a suspension containing a drug to be tested through the micro flow chamber;

(b) further providing living cells responsive to the drug in the micro flow chamber in contact with or in the immediate vicinity of the silicon semiconductor electrode;

(c) contacting the living cells with the drug to be tested by flowing a solution or suspension of the drug to be tested through the micro flow chamber; and (d) repetitively stopping the flow and repetitively measuring the change in pH of the solution or suspension about said living cells when the flow is stopped by means of the silicon semiconductor electrode to measure any change in pH caused by the drug interacting with the living cells so as to screen for the presence or activity of the drug.

3. A method for detecting a toxic substance comprising:

(a) providing a micro flow chamber having a height of between about 50 μm and 200 μm and wherein a portion of the micro flow chamber is a silicon semiconductor electrode, the micro flow chamber being adapted for continuous or intermittent flow of a solution or suspension suspected of containing a toxic substance;

(b) further providing living cells responsive to the toxic substance being tested in the micro flow chamber in contact with or in the immediate vicinity of the silicon semiconductor electrode;

(c) contacting the living cells with the solution or suspension suspected of containing the toxic substance by flowing the solution or suspension through the micro flow chamber and; and (d) repetitively stopping the flow and repetitively measuring the change in pH of the solution or suspension about said living cells when the flow is stopped by means of the silicon semiconductor electrode so as to detect the presence of the toxic substance.

* * * * *